(12) United States Patent
Li et al.

(10) Patent No.: US 7,306,827 B2
(45) Date of Patent: Dec. 11, 2007

(54) METHOD AND MACHINE FOR REPLICATING HOLOGRAPHIC GRATINGS ON A SUBSTRATE

(75) Inventors: Peter Y. Li, Andover, MA (US); Jean Qiu, Andover, MA (US); Alex Borsody, Lowell, MA (US)

(73) Assignee: SRU Biosystems, Inc., Woburn, MA (US)

( * ) Notice: Subject to any disclaimer, the term of this patent is extended or adjusted under 35 U.S.C. 154(b) by 1050 days.

(21) Appl. No.: 10/201,818

(22) Filed: Jul. 23, 2002

(65) Prior Publication Data

US 2003/0017581 A1 Jan. 23, 2003

Related U.S. Application Data

(63) Continuation-in-part of application No. 10/196,058, filed on Jul. 15, 2002, and a continuation-in-part of application No. 10/180,374, filed on Jun. 26, 2002, now Pat. No. 7,023,544, and a continuation-in-part of application No. 10/180,647, filed on Jun. 26, 2002, which is a continuation-in-part of application No. 10/059,060, filed on Jan. 28, 2002, now Pat. No. 7,070,987, and a continuation-in-part of application No. 10/058,626, filed on Jan. 28, 2002, now Pat. No. 6,951,715, which is a continuation-in-part of application No. 09/930,352, filed on Aug. 15, 2001.

(60) Provisional application No. 60/303,028, filed on Jul. 3, 2001, provisional application No. 60/283,314, filed on Apr. 12, 2001, provisional application No. 60/244,312, filed on Oct. 30, 2000.

(51) Int. Cl.
*B05D 3/06* (2006.01)
*B05D 3/12* (2006.01)

(52) U.S. Cl. .................. 427/264; 427/359; 427/372.2; 427/407.1

(58) Field of Classification Search .............. 427/264
See application file for complete search history.

(56) References Cited

U.S. PATENT DOCUMENTS

| 3,689,346 A | 9/1972 | Rowland .................... 156/245 |
|---|---|---|
| 3,810,688 A | 5/1974 | Ballman et al. ............. 350/96 |
| 3,856,404 A | 12/1974 | Hershler et al. |
| 3,856,604 A | 12/1974 | Hershler et al. ............ 156/361 |
| 4,009,933 A | 3/1977 | Firester ..................... 350/152 |
| 4,050,895 A | 9/1977 | Hardy et al. ................ 436/527 |
| 4,240,751 A | 12/1980 | Linnecke et al. ........... 356/409 |
| 4,289,371 A | 9/1981 | Kramer ..................... 350/3.71 |
| 4,344,438 A | 8/1982 | Schultz ...................... 128/633 |
| 4,420,502 A | 12/1983 | Conley ..................... 427/54.1 |
| 4,536,608 A | 8/1985 | Sheng et al. ................ 136/259 |
| 4,560,248 A | 12/1985 | Cramp et al. ................ 385/12 |
| 4,576,850 A | 3/1986 | Martens ...................... 428/156 |
| 4,608,344 A | 8/1986 | Carter et al. ................. 436/34 |
| 4,650,329 A | 3/1987 | Barrett et al. ............... 356/481 |
| 4,652,290 A | 3/1987 | Cho et al. ....................... 65/31 |
| 4,668,558 A | 5/1987 | Barber ....................... 428/156 |
| 4,701,008 A | 10/1987 | Richard et al. ............. 385/132 |
| 4,810,658 A | 3/1989 | Shanks et al. .............. 436/172 |
| 4,815,843 A | 3/1989 | Tiefenthaler et al. ....... 356/128 |
| 4,818,710 A | 4/1989 | Sutherland et al. ......... 436/527 |
| 4,857,273 A | 8/1989 | Stewart et al. ................ 436/82 |
| RE33,064 E | 9/1989 | Carter ......................... 436/34 |
| 4,876,208 A | 10/1989 | Gustafson et al. |
| 4,882,288 A | 11/1989 | North et al. ................. 436/525 |
| 4,888,260 A | 12/1989 | Cowen .......................... 430/1 |
| 4,931,384 A | 6/1990 | Layton et al. .................. 435/7 |
| 4,952,056 A | 8/1990 | Tiefenthaler ................ 356/73.1 |
| 4,958,895 A | 9/1990 | Wells et al. .............. 350/96.12 |
| 4,992,385 A | 2/1991 | Godfrey ..................... 436/525 |
| 4,999,234 A | 3/1991 | Cowan ....................... 428/156 |
| 5,071,248 A | 12/1991 | Tiefenthaler et al. ....... 356/128 |
| 5,118,608 A | 6/1992 | Layton et al. .............. 435/7.1 |
| 5,155,785 A | 10/1992 | Holland et al. ............... 385/89 |
| 5,156,785 A | 10/1992 | Zdrahala .................... 264/108 |
| 5,170,448 A | 12/1992 | Ackley et al. ................ 385/31 |
| 5,175,030 A | 12/1992 | Lu et al. ...................... 428/30 |
| 5,210,404 A | 5/1993 | Cush et al. .................. 250/216 |
| 5,229,614 A | 7/1993 | Andersson et al. ..... 250/370.12 |
| 5,242,828 A | 9/1993 | Bergström et al. .......... 435/291 |
| 5,268,782 A | 12/1993 | Wenz et al. ................... 359/81 |
| 5,310,686 A | 5/1994 | Sawyers et al. |
| 5,337,183 A | 8/1994 | Rosenblatt ................... 359/248 |
| 5,413,884 A | 5/1995 | Koch et al. ..................... 430/5 |
| 5,442,169 A | 8/1995 | Kunz ..................... 250/227.21 |
| 5,455,178 A | 10/1995 | Fattinger .................... 436/164 |
| 5,475,780 A | 12/1995 | Mizrahi ....................... 385/37 |
| 5,478,527 A | 12/1995 | Gustafson et al. ............ 422/82 |
| 5,478,756 A | 12/1995 | Gizeli et al. ................ 436/527 |

(Continued)

FOREIGN PATENT DOCUMENTS

CA 2394966 2/2001

(Continued)

OTHER PUBLICATIONS

Liu, et al., "Development of an optical fiber lactate sensor", Mikrochimica Acta, 1999, 131(1-2), pp. 129-135.

(Continued)

*Primary Examiner*—William Phillip Fletcher, III
(74) *Attorney, Agent, or Firm*—McDonnell Boehnen Hulbert & Berghoff LLP

(57) ABSTRACT

A machine and process for a pattern, such as a submicron grating pattern onto a substrate.

20 Claims, 22 Drawing Sheets

U.S. PATENT DOCUMENTS

| | | | |
|---|---|---|---|
| 5,492,840 A | 2/1996 | Malmqvist et al. | |
| 5,496,701 A | 3/1996 | Pollard-Knight | 435/7.4 |
| 5,559,338 A | 9/1996 | Elliott et al. | 250/492.1 |
| 5,598,267 A | 1/1997 | Sambles et al. | 356/369 |
| 5,598,300 A | 1/1997 | Magnusson et al. | 359/566 |
| 5,606,170 A | 2/1997 | Saaski et al. | 250/458.1 |
| 5,615,052 A | 3/1997 | Doggett | 359/811 |
| 5,629,214 A | 5/1997 | Crosby | 436/518 |
| 5,631,171 A | 5/1997 | Sandstrom et al. | 436/518 |
| 5,690,894 A | 11/1997 | Pinkel et al. | 422/68.1 |
| 5,691,846 A | 11/1997 | Benson, Jr. et al. | 359/530 |
| 5,732,173 A | 3/1998 | Bylander et al. | 385/49 |
| 5,738,825 A | 4/1998 | Rudigier et al. | 422/82 |
| 5,768,461 A | 6/1998 | Svetkoff et al. | 385/116 |
| 5,771,328 A | 6/1998 | Wortman et al. | 385/146 |
| 5,792,411 A | 8/1998 | Morris et al. | 264/400 |
| 5,801,390 A | 9/1998 | Shiraishi | 250/559.3 |
| 5,804,453 A | 9/1998 | Chen | 436/518 |
| 5,814,516 A | 9/1998 | Vo-Dinh | 435/287.2 |
| 5,814,524 A | 9/1998 | Walt et al. | 436/514 |
| 5,821,343 A | 10/1998 | Keogh | |
| 5,846,843 A | 12/1998 | Simon | 436/527 |
| 5,864,641 A | 1/1999 | Murphy et al. | 385/12 |
| 5,922,550 A | 7/1999 | Everhart et al. | 435/7.21 |
| 5,925,878 A | 7/1999 | Challener | 250/225 |
| 5,955,335 A | 9/1999 | Thust et al. | |
| 5,955,378 A | 9/1999 | Challener | 436/525 |
| 5,986,762 A | 11/1999 | Challener | 356/375 |
| 5,991,480 A | 11/1999 | Kunz et al. | 385/37 |
| 5,994,150 A | 11/1999 | Challener et al. | 436/518 |
| 5,998,298 A | 12/1999 | Fleming et al. | 438/692 |
| 6,035,089 A | 3/2000 | Grann et al. | 385/129 |
| 6,042,998 A | 3/2000 | Brueck et al. | 430/316 |
| 6,052,213 A | 4/2000 | Burt et al. | 359/237 |
| 6,076,248 A | 6/2000 | Hoopman et al. | 29/527.1 |
| 6,088,505 A | 7/2000 | Hobbs | 385/147 |
| 6,100,991 A | 8/2000 | Challener | 356/445 |
| 6,128,431 A | 10/2000 | Siminovitch | 385/147 |
| 6,146,593 A | 11/2000 | Pinkel et al. | 422/68.1 |
| 6,174,677 B1 | 1/2001 | Vo-Dinh | 435/6 |
| 6,185,019 B1 | 2/2001 | Hobbs et al. | 359/30 |
| 6,200,737 B1 | 3/2001 | Walt et al. | 430/320 |
| 6,215,928 B1 | 4/2001 | Friesem et al. | 385/37 |
| 6,218,194 B1 | 4/2001 | Lyndin et al. | 436/518 |
| 6,235,488 B1 | 5/2001 | Tom-Moy et al. | |
| 6,303,179 B1 | 10/2001 | Koulik et al. | |
| 6,316,153 B1 | 11/2001 | Goodman et al. | 430/8 |
| 6,320,991 B1 | 11/2001 | Challener et al. | 385/12 |
| RE37,473 E | 12/2001 | Challener | 250/225 |
| 6,338,968 B1 | 1/2002 | Hefti | 436/518 |
| 6,340,598 B1 | 1/2002 | Herron et al. | 436/518 |
| 6,346,376 B1 | 2/2002 | Sigrist et al. | 435/5 |
| 6,377,721 B1 | 4/2002 | Walt et al. | 385/12 |
| 6,404,554 B1 | 6/2002 | Lee et al. | 359/576 |
| 6,449,097 B1 | 9/2002 | Zhu et al. | 359/576 |
| 6,558,957 B1 | 5/2003 | Roinestad et al. | 436/164 |
| 6,570,657 B1 | 5/2003 | Hoppe et al. | 356/445 |
| 6,579,673 B2 | 6/2003 | McGrath et al. | 435/5 |
| 6,587,276 B2 | 7/2003 | Daniell | 359/622 |
| 6,661,952 B2 | 12/2003 | Simpson et al. | 385/37 |
| 6,707,561 B1 | 3/2004 | Budach et al. | 356/521 |
| 6,748,138 B2 | 6/2004 | Wang et al. | 385/37 |
| 6,902,703 B2 | 6/2005 | Marquiss et al. | |
| 2002/0018610 A1 | 2/2002 | Challener et al. | 385/12 |
| 2002/0123050 A1 | 9/2002 | Poponin | |
| 2002/0127565 A1 | 9/2002 | Cunningham et al. | |
| 2002/0135752 A1 | 9/2002 | Sokolov et al. | |
| 2002/0168295 A1 | 11/2002 | Cunningham et al. | |
| 2002/0171045 A1 | 11/2002 | Perraut | |
| 2003/0003599 A1 | 1/2003 | Wagner et al. | |
| 2003/0017580 A1 | 1/2003 | Cunningham et al. | |
| 2003/0017581 A1 | 1/2003 | Li et al. | |
| 2003/0026891 A1 | 2/2003 | Qiu et al. | |
| 2003/0027327 A1 | 2/2003 | Cunningham et al. | |
| 2003/0027328 A1 | 2/2003 | Cunningham et al. | |
| 2003/0032039 A1 | 2/2003 | Cunningham et al. | |
| 2003/0059855 A1 | 3/2003 | Cunningham et al. | |
| 2003/0068657 A1 | 4/2003 | Lin et al. | |
| 2003/0077660 A1 | 4/2003 | Pien et al. | |
| 2003/0092075 A1 | 5/2003 | Pepper | |
| 2003/0113766 A1 | 6/2003 | Pepper et al. | |
| 2003/0148542 A1 | 8/2003 | Pawlak | |
| 2003/0210396 A1 | 11/2003 | Hobbs et al. | 356/416 |
| 2004/0011965 A1 | 1/2004 | Hodakinson | |
| 2004/0132172 A1 | 7/2004 | Cunningham et al. | |
| 2004/0132214 A1 | 7/2004 | Lin et al. | |
| 2004/0151626 A1 | 8/2004 | Cunningham et al. | |

FOREIGN PATENT DOCUMENTS

| | | |
|---|---|---|
| CA | 2395318 | 2/2001 |
| CA | 2394966 | 8/2001 |
| CA | 2395318 | 8/2001 |
| CH | 669050 A5 | 2/1989 |
| CH | 670521 A5 | 6/1989 |
| EP | 0112721 | 7/1987 |
| EP | 0326219 | 1/1989 |
| EP | 0326291 | 8/1989 |
| EP | 0517777 | 12/1992 |
| EP | 0660924 | 7/1995 |
| FR | 2801977 | 12/1999 |
| GB | 2156970 A | 10/1985 |
| GB | 2227089 | 7/1990 |
| WO | 8100912 | 4/1981 |
| WO | 0075353 | 3/1983 |
| WO | 8402578 | 7/1984 |
| WO | 8607149 | 12/1986 |
| WO | 9008318 | 7/1990 |
| WO | 9113339 | 9/1991 |
| WO | 9204653 | 3/1992 |
| WO | 9221768 | 12/1992 |
| WO | 9314392 | 7/1993 |
| WO | 9503538 | 2/1995 |
| WO | 9857200 | 12/1998 |
| WO | 9909392 | 2/1999 |
| WO | 9909396 | 2/1999 |
| WO | 9954714 | 10/1999 |
| WO | 9966330 | 12/1999 |
| WO | 0023793 | 4/2000 |
| WO | 0029830 | 5/2000 |
| WO | 0104697 | 1/2001 |
| WO | WO 02/061429 | 8/2002 |

OTHER PUBLICATIONS

*Corning Inc.* v. *SRU Biosystems, Inc.*, Memorandum Opinion dated Nov. 15, 2005 in the United States District Court for the district of Delaware.

Haidner, "Zero-Order Gratings Used as an Artificial Distributed Index Medium", *Optik*, Wissenschaftlich Verlag GmbH, Stuttgart, DE, vol. 89, No. 3, pp. 107-112, 1992.

Peng, et al., "Experimental Demonstration of Resonant Anomalies in Diffraction from two-Dimensional Gratings", *Optics Letters, Optical Society of America*, vol. 21, No. 9, pp. 549-551, 1996.

Wilson, et al., "The Optical Properties 1-19 of 'Moth Eye' Antireflection Surfaces", *Optical ACTA*, vol. 29, No. 7, pp. 993-1009, 1982.

Bagnich, et al., "*Tunable Optical Filter*", SU 1465855, Derwent Publications, English Translation, Abstract Only, Derwent Publications Ltd.

Magnusson, et al., "New Principal for Optical Filters", *Appl. Phys. Letters*, 61(9) p. 1022-1024 (1992).

Neuschafer et al., "Evanescent Resonator Chips: A Universal Platform with Superior Sensitivity for Fluorescent-based Microarrays", *Biosensors and Bioelectronics*, 18:489-497 (2003).

Budach, et al. "Generation of Transducers for Fluorenscent Based Microarrays with Enhanced Sensitivity and Their Application for Gene Expression Profiling", *Analytical Chemistry*, 2003, 75(11):2571-7.

Nellen, et al., "Integrated Optical Input Grating Couplers as Biochemical Sensors", *Sensors and Actuators*, 15 (1988) 285-295.

W. Lukosz and K. Tiefenthaler, "Embossing technique for fabricating integrated optical components in hard inorganic waveguiding materials," *Optics Letters*, vol. 8, pp. 537-539 (1983).

K. Tiefenthaler and W. Lukosz, "Integrated optical switches and gas sensors," *Optics Letters*, vol. 10, pp. 137-139 (1984).

Chabay, "Optical Waveguides," *Analytical Chemistry*, vol. 54, pp. 1071A-1080A (1982).

Sutherland et al., "Optical Detection of Antibody-Antigen Reactions at a Glass-Liquid Interface," *Clin. Chem.*, vol. 30, pp. 1533-1538 (1984).

Ronald T. Holm and Edward D. Palik, "Internal-reflection spectroscopy," *Laser Focus*, vol. 15, pp. 60-65 (Aug. 1979).

N.J. Harrick and George I. Loeb, "Multiple Internal Reflection Fluorescence Spectrometry," *Analytical Chemistry*, vol. 45, pp. 687-691 (1973).

P.K. Tien, "Light Waves in Thin Films and Integrated Optics," *Applied Optics*, vol. 10, pp. 2395-2413 (1971).

Dakss, et. al., "Grating Coupler for Efficient Excitation of Optical Guided Waves in Thin Films," *Applied Physics Letters*, vol. 16, pp. 523-525 (1970).

Sutherland et al., "Immunoassays at a Quartz-Liquid Interface: Theory, Instrumentation and Preliminary Application to the Fluorescent Immunoassay of Human Immunoglobulin G," *Journal of Immunological Methods*, vol. 74, pp. 253-265 (1984).

English translation of CH 670 521 A5.

English translation of CH 669 050 A5.

Anderson, et al., "Proteomics: applications in basic and applied biology", *Current Opinion in Biotechnology*, 2000, 11:408-412.

MacBeath, et al., "Printing Proteins as Microarrays for High-Throughput Function Determination", *Science*, vol. 289, pp. 1760-1763, 2000.

deWildt, et a., "Antibody arrays for high-throughput screening of antibody-antigen interactions", *Nature Biotechnology*, vol. 18, pp. 989-994, 2000.

Cunningham, et al., "A plastic colorimetric resonant optical biosensor for multiparallel detection of label-free biochemical interactions", *Sensors and Actuators B*, 85 (2002) 219-226.

Caruso, et al., "Quartz Crystal Microbalance Study of DNA Immobilization and Hybridization for Nucleic Acid Sensor Development", *Analytical Chemistry*, vol. 69, No. 11, pp. 2043-2049, 1997.

Hefti, et al, "Sensitive detection method of dielectric dispersions in aqueous-based, surface-bound macromolecular structures using microwave spectroscopy", *Applied Physics Letters*, vol. 75, No. 12, pp. 1802-1804, 1999.

Wu, et al., "Bioassay of prostate-specific antigen (PSA) using microcantilevers", *Nature Biotechnology*, vol. 19, pp. 856-860, 2001.

Wasserman, et al., "Structure and Reactivity of Alkylsiloxane Monolayers Formed by Reaction of Alkyltrichlorosilanes on Silicon Substrates", *Langmuir*, 5, 1074-1087, 1989.

Kallury, et al., "X-ray Photoelectron Spectroscopy of Silica Surfaces Treated with Polyfunctional Silanes", *Anal. Chem.*, 60, 169-172, 1988.

Cunningham, et al., "Colorimetric resonant reflection as a direct biochemical assay technique", *Sensors and Actuators B*, 81 (2002) 316-328.

Mullaney, et al., "Epitope Mapping of Neutralizing Botulinum Neurotoxin A Antibodies by Phage Display", *Infection and Immunity*, vol. 69, No. 10, pp. 6511-6514, 2001.
Neuschafer et al., Evanescent resonator chips: a universal platform with superior sensitivity for fluorescence-based microarrays. Biosensors & Bioelectronics, 18 (2003) 489-497.
Budach et al., Generation of transducers for fluorescence-based microarrays with enhanced sensitivity and their application for gene expression profiling. Analytical Chemistry. Jun. 1, 2003;75(11):2571-7.
U.S. Appl. No. 09/929,957, filed Aug. 15, 2001.
U.S. Appl. No. 09/930,352, filed Aug. 15, 2001.
U.S. Appl. No. 10/415,037, filed Oct. 23, 2001.
U.S. Appl. No. 10/399,940, filed Oct. 23, 2001.
U.S. Appl. No. 10/059,060, filed Jan. 28, 2002.
U.S. Appl. No. 10/201,818, filed Jul. 23, 2002.
U.S. Appl. No. 10/237,641, filed Sep. 9, 2002.
U.S. Appl. No. 10/277,908, filed Aug. 26, 2002.
U.S. Appl. No. 10/233,730, filed Sep. 3, 2002.
U.S. Appl. No. 10/180,374, filed Jun. 26, 2002.
U.S. Appl. No. 10/180,647, filed Jun. 26, 2002.
U.S. Appl. No. 10/253,846, filed Sep. 25, 2002.
U.S. Appl. No. 10/196,058, filed Jul. 15, 2002.
U.S. Appl. No. 10/667,696, filed Sep. 22, 2003.
U.S. Appl. No. 10/058,626, filed Jan. 28, 2002.
Lenau, Torben; *Material, Silicon Nitride*, 1996, 97, 98.
Cerac, Technical publications: *Tantalum Oxide, $Ta_2O_5$ for Optical Coating*, 2000, Cerac, Inc.
Cunningham et al., *Sensors and Actuators* B 85; pp. 219-226 (2002).
Cunningham et al., *Sensors and Actuators* B 81; pp. 316-328 (2002).
Pandey, A. and Mann, M., *Nature.* 405(6788):837-46 (2000).
Patterson, S.D., *Current Opinions in Biotechnology*, 11(4):413-8 (2000).
International Search Report for foreign counterpart application PCT/US03/01175.
Cowan, "The Recording and Large Scale Replication of Crossed Holographic Grating Arrays using Multiple Beam Interferometry", SPIE, vol. 503, *Application, Theory, and Fabrication of Periodic Structures*, pp. 120-129 (1984).
Cowan, "Holographic honeycomb microlens", vol. 24, No. 5, *Optical Engineering*, pp. 796-802 (1985).
Cowan, et al., "The Recording and Replication of Holographic Micropatterns for the Ordering of Photographic Emulsion Grains in Film Systems", vol. 31, No. 3, *J. Imaging Sci.*, pp. 100-107 (1987).
Wang, et al., "Guided-mode Resonances in Planar Dielectric-Layer Diffraction Gratings", vol. 7, No. 8, *J. Opt. Soc. Am.*, pp. 1470-1474 (1990).
Cowan, "Aztec Surface-Relief Volume Diffractive Strucutre", vol. 7, No. 8, *J. Opt. Soc. Am.*, pp. 1529-1544 (1990).
Patel, et al., "Multiwavelength Tunable Liquid-Crystal Etalon Filler", vol. 3, No. 7, *IEEE Photonics Technology Letters*, pp. 643+-644 (1991).
Patel, et al., "Electrically Tunable and Polarization Insensitive Fabry-Perot etalon with a Liquid-Crystal Film", vol. 58, No. 22, *American Institute of Physics*, pp. 2491-2493 (1991).
Magnusson, et al., "Direct Optical Immunosensing (Sensitivity and Selectivity)", *Sensor and Actuators B*, 6, pp. 122-126 (1992).
Wang, et al., "Theory and Applications of Guided-Mode Resonance Filters", vol. 32, No. 14, *Applied Optics*, pp. 2606-2613 (1993).
Wang, et al., "Design of Waveguide-Grating Filters with Symmetrical Line Shapes and Low Sidebands", vol. 19, No. 12, *Optical Society of America*, pp. 919-921 (1994).
Jin, et al., "A Biosensor Concept Based on Imaging Ellipsometry for Visualization of Biomolecular Interactions", 232, *Analytical Biochemistry*, p. 69-72 (1995).
Brecht, et al., "Optical Probes and Transducers", vol. 10, *Biosensors & Bioelectronics*, pp. 923-936 (1995).
Magnusson, et al., "Transmission Bandpass Guided-Mode Resonance Filters", vol. 34, No. 35, *Applied Optics*, pp. 8106-8109 (1995).
Peng, et al., "Experiemental Demonstration of Resonant Anomalies in Diffraction from Two-Dimensional Gratings", vol. 21, No. 8, *Optics Letters*, pp. 549-551 (1996).
Sigal, et al., "A Self-Assembled Monolayer for the Binding and Study of Histidine-Tagged Proteins by Surface Plasmon Resonance", vol. 68, No. 3, *Analytical Chemistry*, pp. 490-497 (1996).
Peng, et al., "Resonant Scattering from Two-Dimonsional Gratings", vol. 13, No. 5, *J. Opt. Soc. Am. A.*, pp. 993-1005 (1996).
Jordan, et al., "Surface Plasmon Resonance Imaging Measurements of Electrostatic Biopolymer Adsorption onto Chemically modified Gold Surfaces", vol. 69, No. 7, *Analytical Chemistry*, pp. 1449-1456 (1997).

Raguin, et al., "Structured Surfaces Mimic Coating Performance", *Laser Focus World*, pp. 113-117 (1997).

Lin, et al., "A Porous Silicon-Based Optical Interferometric Biosensor", vol. 278, *Science*, pp. 840-843 (1997).

Morhard, et al., Immobilization of Antibodies in Micropatterns for Cell Detection by Optical Diffraction, *Sensors and Actuators B 70*, pp. 232-242 (2000).

Jenison, et al., "Interference-Based Detection of Nucleic Acid Targets on Optically Coated Silicon", vol. 19, *Nature Biotechnology*, pp. 62-64 (2001).

Cunningham, et al., U.S. Provisional Patent Application, "*Resonant Reflection Microarray*", U.S. Appl. No. 60/244,312, filed Oct. 30, 2000.

Cunningham, et al., U.S. Provisional Patent Application, "*Resonant Reflection Microarray*", U.S. Appl. No. 60/283,314, filed Apr. 12, 2001.

Cunningham, et al., U.S. Provisional Patent Application, "*Resonant Reflection Microarray*", U.S. Appl. No. 60/303,028, filed Jul. 3, 2001.

Hobbs, et al., "Automated Interference Lithography Systems for Generation of Sub-Micron Feature Size Patterns", *SPIE*, vol. 3879, pp. 124-135, Sep. 1999.

Cunningham, "Introduction to Bioanalytical Sensors", *Techniques in Analytical Chemistry*, pp. 260-291.

Challener, et al., "A Multiplayer Grating-Based Evanescent Wave Sensing Technique", *Elsevier Science B.B.*, pp. 42-46 (2000).

Huber, et al., "Direct Optical Immunosensing (Sensitivity and Selectivity)", *Sensors and Actuators B*, 6, pp. 122-126 (1992).

Invitation to Pay Additional Fees in foreign counterpart application PCT/US01/50723.

Statement of Applicants dated May 4, 2004.

Bertoni, et al., "Frequency-Selective Reflection and Transmission by a Periodic Dielectric Layer", *IEEE Transactions on Antennas and Propagation*, vol. 37, No. 1, pp. 78-83 (1989).

Brundrett, et al., "Normal-incidence guided-mode resonant grating filters: design and experimental demonstration", *Optics Letters*, vol. 23, No. 9, pp. 700-702 (1998).

Peng, "*Polarization-control Components and Narrow-band Filters Based on Subwavelength Grating Structures*" 1996.

Amine
- Sulfo-succinimidyl-6-(biotinamido)hexanoate (Sulfo-NHS-LC-Biotin)
  - Streptavidin / avidin then biotinylated molecule
- N,N'-disuccinimidyl carbonate (DSC); • -$NH_2$, non-cleavable
- Dimethyl pimelimidate (DMP); • -$NH_2$, non-cleavable
- Dimethyl 3,3'-dithiobispropionimidate (DTBP); • -$NH_2$, cleavable
- 1-Ethyl-3-(3-Dimethylaminopropyl)carbodiimide Hydrochloride (EDC) and N-Hydroxysulfosuccinimide (Sulfo-NHS); • -COOH
- Sulfo-succinimidyl 6-[a-methyl-a-(2-pyridyl-dithio)toluamido] hexanoate (Sulfo-LC-SMPT); • -SH, cleavable
- N-(B-Maleimidopropyloxy)succinimide ester (BMPS)
  - -$SH_2$, non-cleavable
- Sulfo-succinimidyl 4-[N-maleimidomethyl)cyclohexane-1-carboxylate (Sulfo-SMCC); • -SH, non-cleavable Aldehyde
- Directly with aldehyde or first amino then aldehyde
  - -$NH_2$ Ni(II)
- Using Nitrilotriacetic acid (NTA) group, which forms a chelate with Ni(II)
  - His-tagged molecules

Concentric Circle Design

Hexagonal Grating Design

METHOD AND MACHINE FOR REPLICATING HOLOGRAPHIC GRATINGS ON A SUBSTRATE

PRIORITY

This application is a continuation-in-part of U.S. application Ser. No. 10/180,374, filed Jun. 26, 2002 now U.S. Pat. No. 7,023,544, U.S. application Ser. No. 10/180,647, filed Jun. 26, 2002, and U.S. application Ser. No. 10/196,058 entitled "A Method for Producing a Clorimetric Resonant Reflection Biosensor on Rigid Surfaces" filed Jul. 15, 2002, which are continuations-in-part of U.S. application Ser. No. 10/059,060, filed Jan. 28, 2002 now U.S. Pat. No. 7,070,987 and U.S. application Ser. No. 10/058,626, filed Jan. 28, 2002, now U.S. Pat. No. 6,951,715 which are continuations-in-part of U.S. application Ser. No. 09/930,352, filed Aug. 15, 2001, which claims the benefit of U.S. provisional application 60/244,312 filed Oct. 30, 2000; U.S. provisional application 60/283,314 filed Apr. 12, 2001; and U.S. provisional application 60/303,028 filed Jul. 3, 2001, all of which are incorporated herein in their entirety.

TECHNICAL AREA OF THE INVENTION

The invention also relates to methods and compositions for producing pattern coated substrates including, for example, colorimetric resonant biosensors.

BACKGROUND OF THE INVENTION

Conventional methods of replicating gratings, such as holographic gratings, include injection molding of a plastic part incorporating a grating, or grating replication with a tool in a cylindrical drum format. These methods require significant investment in tool fabrication, and are not flexible to changes in the tool. In laboratory settings, a hand roll process may be used, but it is labor intensive, and the replication products are susceptible to variations related to the manual operation. Methods are needed in the art for replicating patterns, including grating patterns.

SUMMARY OF THE INVENTION

In one principle aspect, the invention provides a machine and process for microreplicating a grating pattern onto a substrate. This and other embodiments of the invention are described below.

Processes of the invention use a machine to perform a step and repeat operation on a substrate. The machine receives a substrate by advancing a substrate roll until a substrate roll section is produced. A coating, for example, an epoxy or resin is applied between the substrate and a tool having a pattern to form a substrate roll section with a coating layer. The pattern on the tool is transferred to the coating layer by rolling a shuttle mechanism over the coating on the substrate to create a pattern coating layer on the substrate. Although the substrate roll is not advanced, the substrate roll section with the coating layer travels with the linear roller causing the substrate roll section with the coating layer to roll and advance over the tool.

As the linear roller advances and causes the substrate roll section to roll over the tool, the tool transfers the pattern to the coating layer to create a pattern coated substrate. A curing process then cures the pattern coating layer on the substrate. Detachment of the cured pattern substrate from the tool is performed, for example, by unrolling the linear roller in order to delaminate the cured pattern substrate from the tool. The above procedures can then be repeated by advancing the substrate roll in order to form another substrate roll section. A high refractive index dielectric film can be applied to the pattern coating layer to provide a dielectric film layer that has a higher refractive index than the substrate.

One embodiment of the invention provides a method for replicating a pattern. The method comprises advancing a substrate supply roll until a substrate roll section is produced; applying a liquid between the substrate roll section and a tool having the pattern to form a substrate roll section with a liquid layer; rolling a shuttle mechanism having a pressure roller such that the substrate roll section with the liquid layer is rolled between the pressure roller and the tool, wherein the shuttle mechanism advances in a direction to cover the tool with the substrate roll section with a liquid layer while the substrate supply roll remains stationary, the pattern on the tool is transferred to the liquid layer to create a pattern coated substrate; hardening the pattern coated substrate to form a cured pattern substrate; and detaching the cured pattern substrate from the tool by retracting the shuttle mechanism while the substrate supply roll remains stationary; and repeating the above steps on a next substrate roll section.

The detachment of the cured pattern substrate from the tool can be by peeling the cured pattern substrate from the tool or by unrolling the pressure roller as the shuttle mechanism retracts wherein the cured pattern substrate is lifted by the pressure roller as the shuttle mechanism retracts.

The pattern can be a grating pattern, which can comprise a predetermined number of rows and a predetermined number of columns. The pattern can be a colorimetric resonant reflectance sensor grating pattern.

The tool can comprise a master wafer having a master wafer grating pattern. The master wafer grating pattern can be substantially flat and the shuttle mechanism can advance and retract substantially in a plane. Alternatively, the master wafer grating pattern is curved and the shuttle mechanism can advance and retract by following the curved master wafer. The master wafer can be a master silicon wafer.

The liquid can be selected from the group consisting of an epoxy, a polymer, a cement and a resin. Alternatively, the liquid can be a solvent free radiation addition polymerizable crosslinkable material such as an acrylate epoxy urethane based material.

The step of hardening the pattern coated substrate can comprise exposing the pattern coated substrate to an electron beam.

The liquid can be an epoxy and the pattern coated substrate can be a pattern epoxy substrate. Hardening the pattern epoxy substrate can comprise exposing the pattern epoxy substrate to ultraviolet light or heat.

The liquid can be an epoxy and applying the epoxy between the substrate roll section can comprise applying the epoxy substantially between the substrate roll section and the grating pattern on the tool.

The substrate supply roll can comprise a substrate material selected from the group consisting of glass, plastic, epoxy, metal, paper, polyurethane, polycarbonate, polyester, composite plastic and glass, composite plastic and metal, and composite plastic and paper. A substrate material roll can comprise at least one liner, which can be removed from the substrate material as the substrate roll is advanced.

The method can comprise advancing the cured pattern substrate onto a take-up spool to form a cured substrate roll while the shuttle mechanism remains stationary.

The pattern can have a periodic spacing wherein the spacing is between 0.1 microns to 2.0 microns. The pattern can be a submicron grating pattern and can have, for example, a periodic spacing wherein the spacing is between 0.2 microns to 0.6 microns.

A film, such as a high refractive index dielectric thin film can be deposited on the cured pattern substrate. The dielectric thin film can have a higher refractive index than the substrate roll section.

Another embodiment of the invention provides a machine comprising a substrate roll on a supply spool wherein the substrate roll is advanced until a substrate roll section is produced, a tool having a pattern for receiving the substrate roll section, an applicator for applying a liquid between the substrate roll section and the tool to form a substrate roll section with a liquid layer, a shuttle mechanism having a pressure roller for rolling over the substrate roll section with the liquid layer wherein the pattern is transferred from the tool to the liquid layer on the substrate roll section to form a pattern coated substrate, and a hardener to harden the pattern coated substrate to form a cured pattern substrate, wherein the cured pattern substrate is detached from the tool.

Even another embodiment of the invention provides a machine comprising an uncoated roll of plastic on a supply spool wherein the uncoated roll of plastic is unrolled until a plastic roll section is formed, a master silicon wafer having a grating pattern for receiving the plastic roll section from the uncoated roll of plastic, an epoxy applicator for applying an epoxy between the plastic roll section and the master silicon wafer to form an epoxy layer on the plastic roll section, a shuttle mechanism having a pressure roller for rolling over the epoxy layer on the plastic roll section while the supply spool remains stationary wherein the grating pattern is transferred from the master silicon wafer to the epoxy layer on the plastic roll section to form a pattern epoxy section as the pressure roller rolls over the epoxy layer on the plastic roll section and the master silicon wafer, and an ultraviolet light to cure the pattern epoxy section to form a cured section. The cured section is peeled from the master silicon wafer by unrolling the shuttle mechanism and the cured section travels with the pressure roller as the cured section is peeled from the master silicon wafer.

BRIEF DESCRIPTION OF THE DRAWINGS

FIG. 11 shows three types of surface activation chemistry (Amine, Aldehyde, and Nickel) with corresponding chemical linker molecules that can be used to covalently attach various types of biomolecule receptors to a biosensor;

FIG. 13A shows a biosensor that is incorporated into a microtitre plate. FIG. 13B shows a biosensor in a microarray slide format;

DETAILED DESCRIPTION OF THE INVENTION

Microreplicated Plastic Grating

Figure 1:
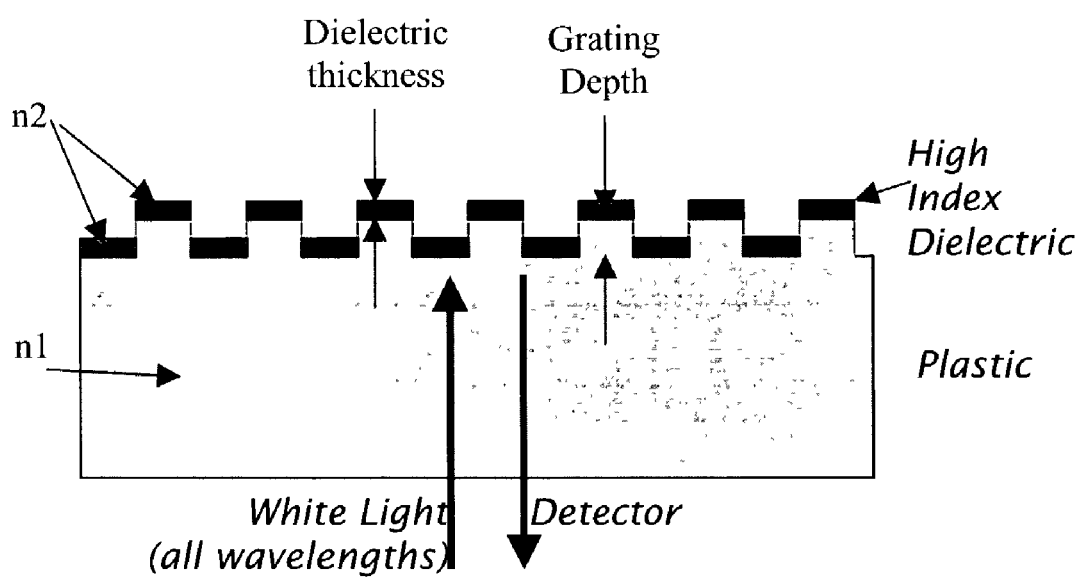
FIG. 1 shows a schematic diagrams of one embodiment of a patterned optical grating structure used for a colormetric resonant reflectance biosensor. $n_1$ represents a grating structure. $n_2$ represents the refractive index of a high refractive index dielectric layer. This figure shows a cross-sectional view of a biosensor wherein light is shown as illuminating the bottom of the biosensor; however, light can illuminate the biosensor from either the top or the bottom.
Figure 2:
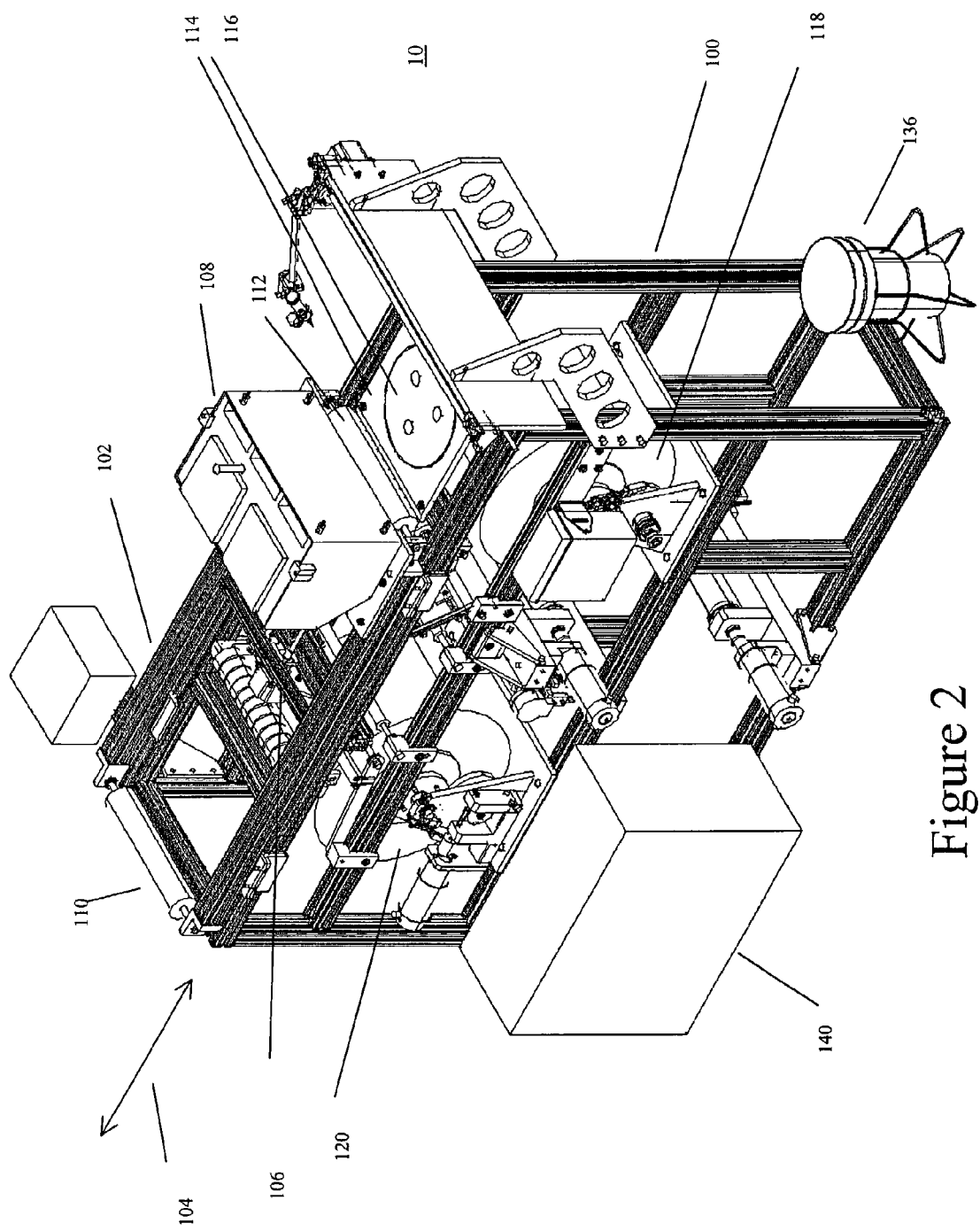
FIG. 2 illustrates a schematic drawing of one embodiment of a replication machine. The movement of the shuttle mechanism 102 is demonstrated at 104. The figure depicts a drive motor 106 for the shuttle mechanism.

A pattern such as an optical grating or other pattern can be inexpensively produced by creating a master structure and then microreplicating the master structure on a plastic sheet, such as a polycarbonate sheet, for example. An optical grating is a grating with a surface structure that when coated with a high refractive index dielectric material acts as a colorimetric resonant diffractive grating. An optical grating is a regular repeating structure such as, for example a pattern of lines, holes, rectangles, posts or other shapes. The master structure can be replicated by curing or hardening a liquid that has the master structure pattern. As one example, optical epoxy or cement can be dispensed between the surface of the master structure and a polycarbonate sheet and then cured by exposure to ultraviolet light, such as light from a xenon lamp. UV-cured resins or other materials can be used as well. Once a pattern is replicated, it can be, for example, coated with a dielectric material having a higher refractive index than the hardened liquid or a reflective material to form, for example, a biosensor, such as a colorimetric resonant reflectance biosensor (See, U.S. application Ser. Nos. 10/058,626 and 10/059,060). Biosensors thus produced can be incorporated into disposable assay formats such as microtiter plates and microarray slides.

A master structure, such as a tool having a pattern, can comprise a master wafer such as a master silicon wafer that can be processed like an integrated circuit. For example, a pattern, such as a grating having a geometric patterns can be produced with sub-micron features using step-and-repeat photolithography similar to the process of manufacturing silicon integrated circuits. Specifically, a reticle with the desired pattern can be used to expose a silicon wafer coated with a very thin layer of photoresist material. Patterns include grating structures with a cross section of a square wave, a triangular wave, a sinusoidal wave, or an inverted "u" shape. Other patterns include gratings comprising a repeating pattern of shapes selected from the group consisting of lines, squares, circles, ellipses, triangles, trapezoids, sinusoidal waves, ovals, rectangles and hexagons. A pattern can also comprise a pattern that vanes sinusoidly in height, a set of concentric rings, see, e.g., FIG. 21, or a three dimensional phase-quantized terraced surface relief pattern whose groove pattern resembles a stepped pyramid. See, e.g., FIG. 23. Other patterns are possible also.

The photoresist can be exposed using deep-UV light. The reticle image can be printed at a 1:1 ratio or reduced by 4:1 or other ratios. Step-and-repeat photolithography produces one fairly small pattern at a time, and then the exposure is repeated for another portion of the wafer. To produce a grating pattern that can be used in a standard format 96-well microtiter plate with 8 rows and 12 columns, for example, the step-and-repeat process described above can be used to create two 108×72 mm grids on a 200 mm wafer. Each grid can comprise 96 7-mm circles that contain a desired pattern.

After developing the exposed photoresist, the pattern can be transferred to a silicon wafer using a reactive ion etch. For example, a reactive ion etch to a depth of about 5 nm to about 10,000 nm can be used. In a preferred embodiment of the invention a depth of about 100 nm to about 500 nm can be used. After etching, the photoresist can be removed.

The pattern in the silicon master structure can be replicated onto the surface of a sheet of polycarbonate or other suitable plastic or material. To replicate the master structure, a UV cured photopolymer such as type SK-9 UV curing optical cement (Summers Optical) can be used. SK-9 exhibits high adhesion to plastic, which is useful in the exemplary embodiment, but other cements or epoxies could be used as well. For example, a bead of optical cement can be applied to a master structure surface. A substrate, such as 0.005" thick polycarbonate sheet, can be placed over the master structure. A roller can be used to evenly spread the optical cement between the silicon master structure and the substrate. An appropriate amount of pressure on the roller can ensure that the cement is pressed into the master structure so that the master will be faithfully reproduced upon curing.

The optical cement can be exposed to UV light through the polycarbonate sheet substrate. About 95 seconds of exposure is adequate with SK-9. Once the replicated pattern is hardened, the substrate can be peeled away from the master structure to form a cured pattern substrate. The cured cement surface (i.e., the surface opposite the substrate) can be coated with a high refractive index material. For example, a layer of silicon nitride with a thickness of about 120 nm can be sputter deposited onto the surface of the cured cement. Other coatings, such as (without limitation) zinc sulfide, titanium dioxide, or tantalum oxide can be sputter deposited onto the cured cement pattern as well. A coated sensor cross section is shown in FIG. 1. Keeping the high refractive index coating relatively thin (e.g., less than or about equal to the grating depth) makes it unnecessary to process the sensor further, such as by photolithographic patterning or etching of the coating. This is because the deposited layer will follow the shape of the replicated grating pattern. Eliminating further sensor processing can greatly simplify the manufacturing process and thus keep sensor costs low.

It is also possible to use a master structure produced as described to produce "daughter" tools by methods such as electroplating nickel replicas, much as compact discs are produced. Further economies can be realized by processing a continuous sheet of substrate material past a master structure "tool". For example, using a continuous film approach to sensor fabrication, a single 1000-foot roll of material can contain several thousand sensors, yielding tremendous cost advantages compared to batch fabrication methods. Moreover, sensors fabricated using this microreplication methods exhibit performance characteristics as good as or better than sensors fabricated using other methods, such as etching high refractive index layers on glass, plastic, or epoxy substrates.

Machine and Method for Microreplicating Optical Gratings on Plastic Film

Figure 8:
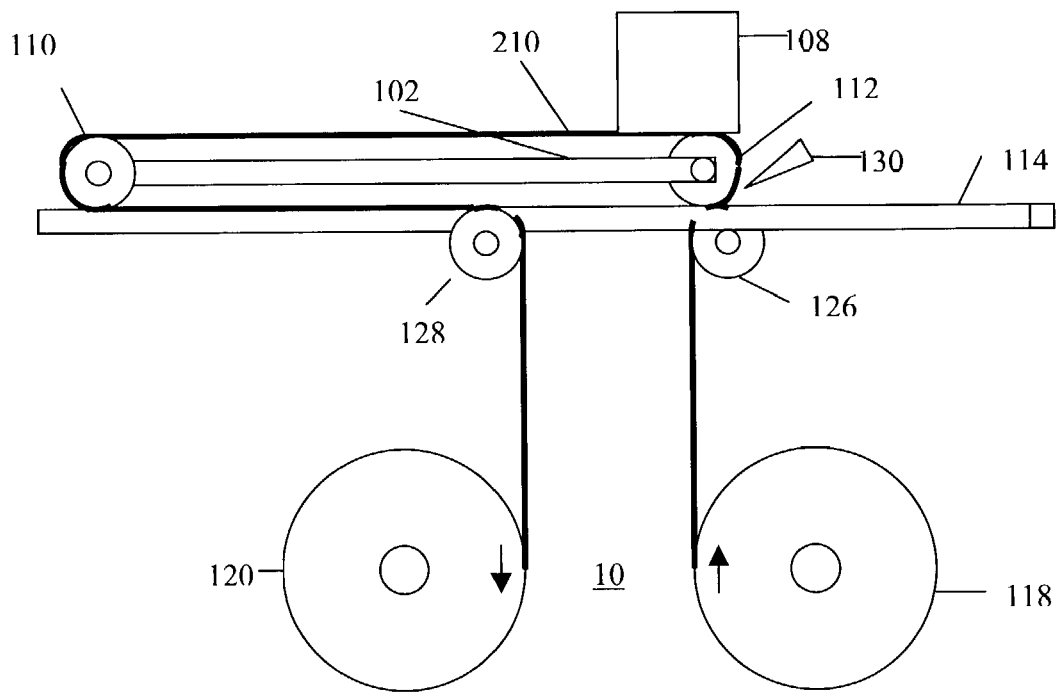
FIG. 8 illustrates a machine 10 for replicating a pattern in a first position.

FIG. 8 illustrates a machine 10 for microreplicating a grating pattern onto a liquid, which is deposited on a substrate material. A substrate supply roll 118 can provides the machine 10 with a substantially continuous supply of rolled substrate material. A substantially continuous supply of rolled substrate material is continuous sheet of substrate material that is a rolled form. Alternatively, the substrate material can be present in a smaller sheet form, i.e., a length of substrate material that is short enough such that is does not need to be rolled-up. Where the substrate is present in a sheet form instead of a roll, a substrate supply sheet is used instead of a substrate supply roll. The substrate supply sheet is advanced to form a substrate sheet section.

The substrate roll 118 can have the substrate material rolled onto a supply spool. As the substrate material unrolls from the substrate roll 118, a section of the unrolled substrate material is produced.

The substrate material feeds around receiving roller 126 and around pressure roller 112 of shuttle mechanism 102. The substrate material continues to feed above shuttle mechanism 102 from pressure roller 112 to shuttle roller 110. The portion of substrate material from the pressure roller 112 to shuttle roller 110 can be referred to as the substrate roll section 210 when the shuttle mechanism is in the position as shown in FIG. 8. The substrate material then runs along the bottom of the shuttle mechanism 102 from roller 110 to second roller 128. Take-up spool 120 then receives the substrate material from second directional roller 128.

Figure 3:
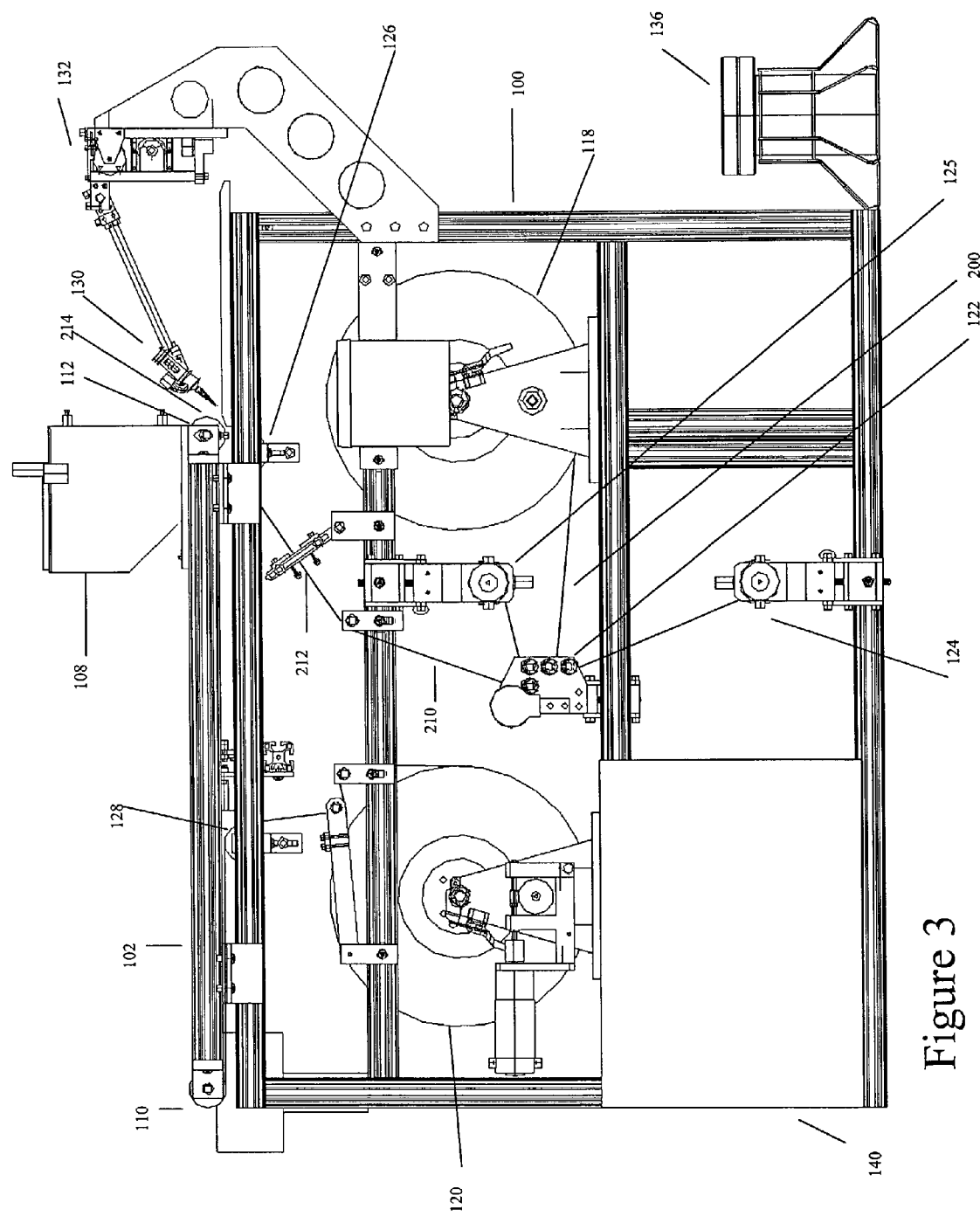
FIG. 3 illustrates a schematic drawing of an embodiment of a replication machine demonstrating, inter alia, an applicator tool 130 and an applicator dispense valve 132.
Figure 4:
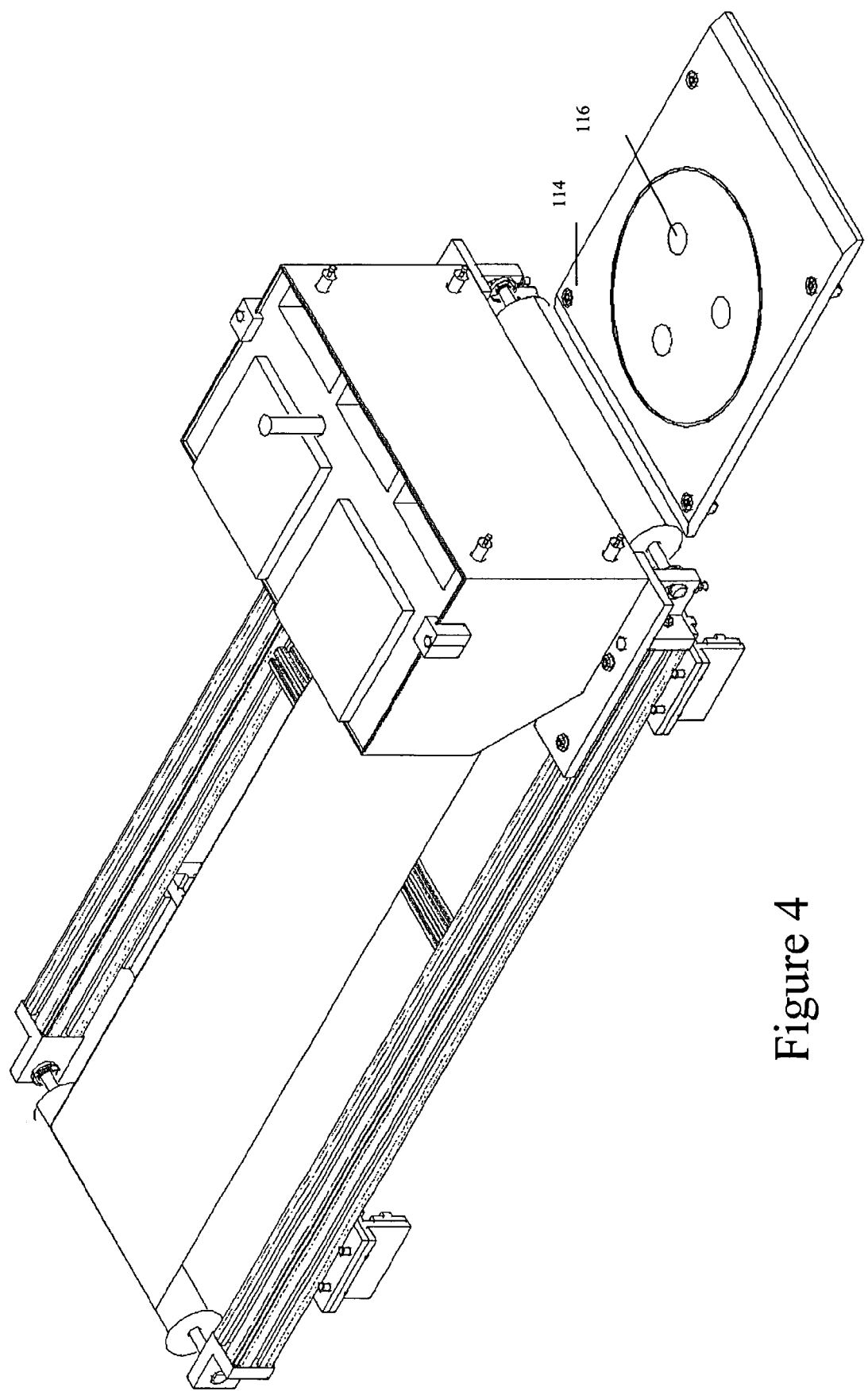
FIG. 4 illustrates a schematic drawing of an embodiment of a replication machine in a first position.

The substrate material can be made of, for example, plastic, polyester, polyurethane, polycarbonate, glass, epoxy, metal, paper, or any other appropriate type of material. The substrate can be a flexible material. Further, the substrate material can by made from any combination of these materials. For example, the substrate can be made from a composite of plastic and glass, plastic and metal, or plastic and paper. Further, the substrate roll 118 can also be made of these materials in rolled form. A substrate material can be about 0.0002 inches to about 0.02 inches thick. In one embodiment of the invention the substrate material comprises at least one liner (e.g., a liner on the bottom or lower surface of the substrate material or a liner on the top or upper surface or both). The liner or liners are removed when, for example, the substrate roll is advanced. FIG. 3 demonstrates a liner removal mechanism 122 and a lower liner take-up spool 124 and an upper liner take-up spool 125.

Figure 9:
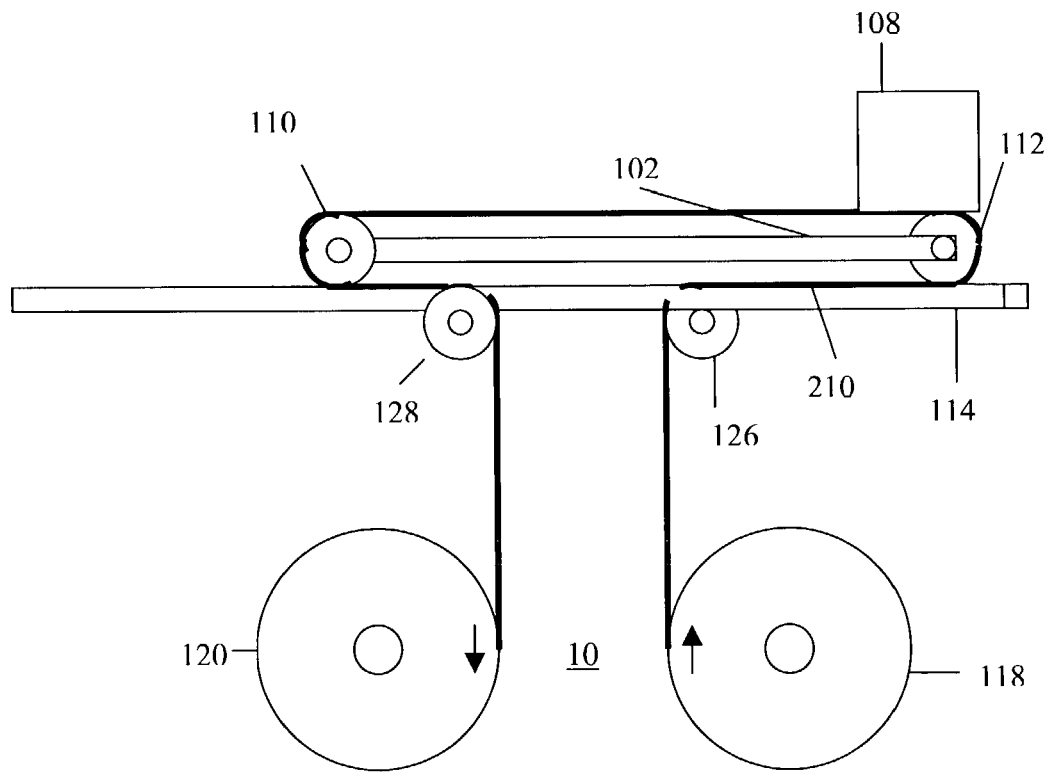
FIG. 9 illustrates the machine 10 in FIG. 8 in a second position.

The shuttle mechanism 102 as shown in FIG. 8 is in an initial position. When the shuttle mechanism 102 is in the initial position, a pressure roller 112 is near the front edge of tool plate 114 when the tool plate 114 is uncovered. The shuttle mechanism 102 then slides over the tool plate 114 from the initial position as shown in FIG. 8 to the end position as shown in FIG. 9. The shuttle mechanism 102 can be driven by, for example, a motor or stepper motor. As the shuttle mechanism 102 advances over the tool plate 114, tool plate 114 receives the substrate roll section 210 from the shuttle mechanism 102.

The tool plate 114 has a tool such as a master wafer with a pattern. The master wafer can be made from silicon, for example, however, other materials can be used. The pattern on the master wafer can be a grating pattern created by photolithography or any appropriate method. The grating pattern can have a predetermined number of rows and a predetermined number of columns. For example, the grating pattern can be a standard format of 96-well microtiter plates with 8 rows and 12 columns each. The pattern for the master wafer can be an array of circular areas of gratings conforming to the bottoms of the 96-well microtiter plates.

Alternatively, the grating pattern for the master wafer can be continuous so that after the pattern is transferred, the grating on the substrate material will be a continuous grating pattern over the substrate material. Accordingly, when the cured pattern substrate is placed onto the bottom of the microtiter plate, then the desired grating will be exposed in the bottom of each of the wells of the microtiter plate.

The machine 10 and method can be used with a grating patterns having a wide range of dimensions. In a preferred embodiment, the periodic spacing on the grating pattern can be between 0.1 microns to 2 microns. Even more preferably, the periodic spacing is sub-micron, that is, less than 1 micron. For example, the periodic spacing between the lines can be between 0.2 to 0.6 microns. In one embodiment, the period of the grating is 550 nm; however a range of about 100 nm to about 1,000 nm can be used, the line width of a grating land area is approximately 275 nm, however a range of about 50 to about 500 nm can be used, and the depth is approximately 200 nm, however a range of about 0.01 micron to about 1 micron can be used. However, other dimensions for the grating pattern can be used. For example, the periodic spacing on the grating pattern can be between 0.01 microns to 5 microns. Alternatively, spacing less than 0.01 microns or greater than 5 microns can be used depending on the specific application without significant loss of the replication system performance.

As discussed in more detail below, the grating pattern can be described as a one-dimensional or two-dimensional, and three-dimensional grating. Accordingly, any reference to a grating contemplates a one-dimensional, two-dimensional, and three-dimensional grating. Additionally, any reference to the periodic spacing between grating lines can apply to one-dimensional, two-dimensional, and three-dimensional gratings.

As is apparent to those who are skilled in the art, the replication method and system described here is applicable to a wide variety of patterns other than grating patterns for biosensor applications. Examples of devices that can be fabricated with the methods and apparatuses of the invention include micro-replicated holograms, holographic optical elements, diffractive lenses, transmission filters and other sub-wavelength structured surfaces (SWS).

Figure 5:
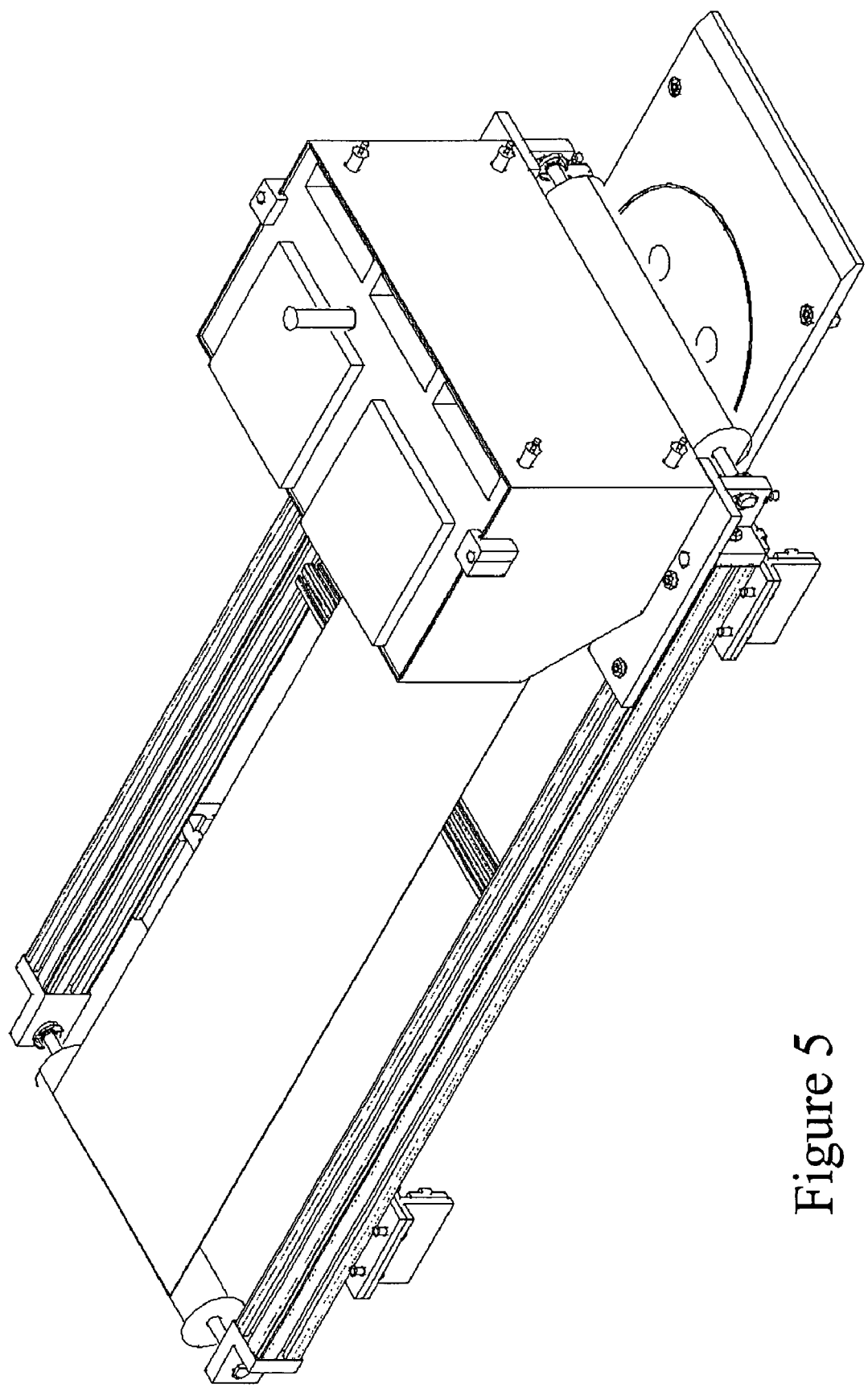
FIG. 5 illustrates a schematic drawing of an embodiment of a replication machine in a second position.
Figure 6:
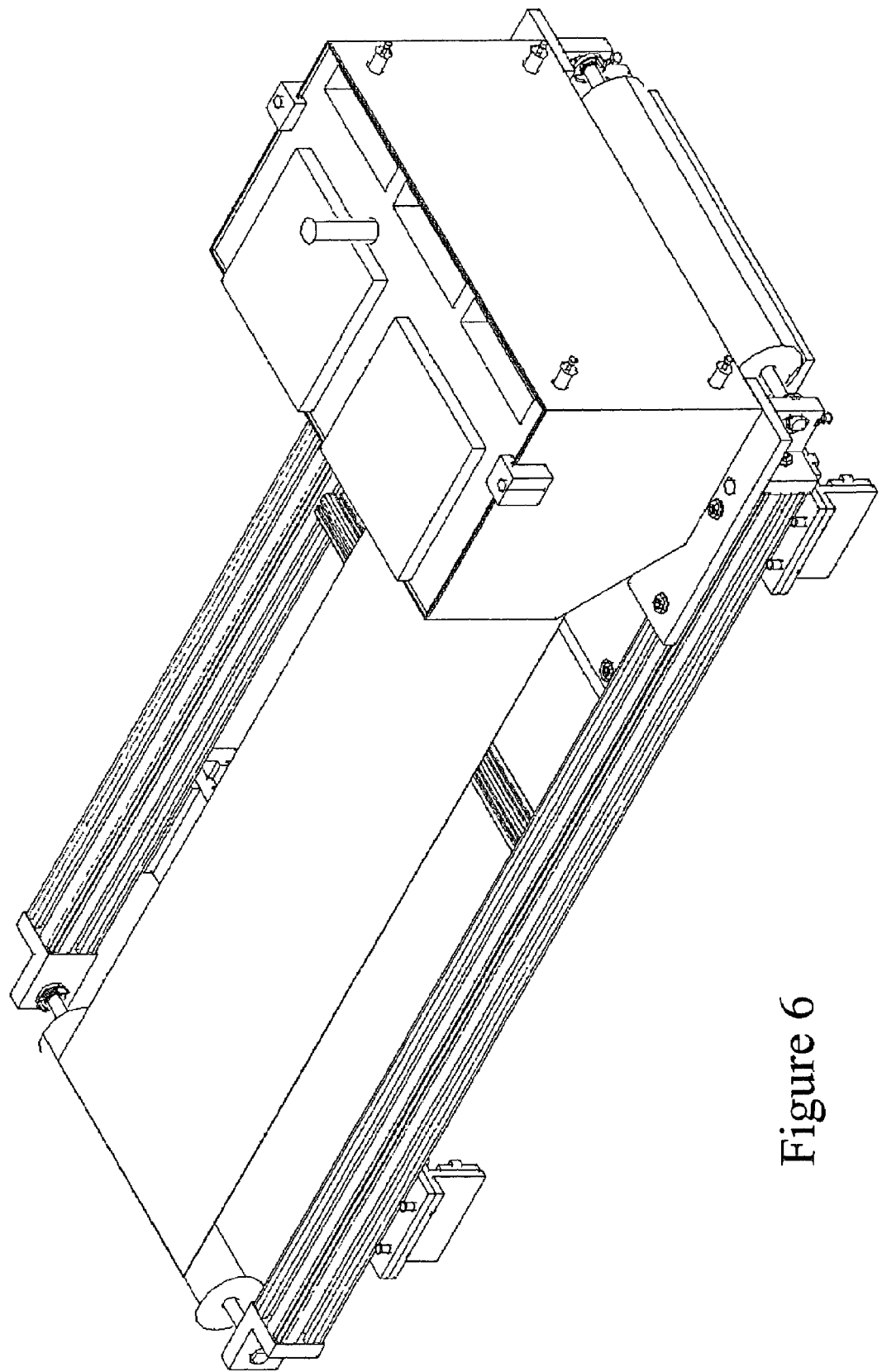
FIG. 6 illustrates a schematic drawing of an embodiment of a replication machine in a third position.
Figure 7:
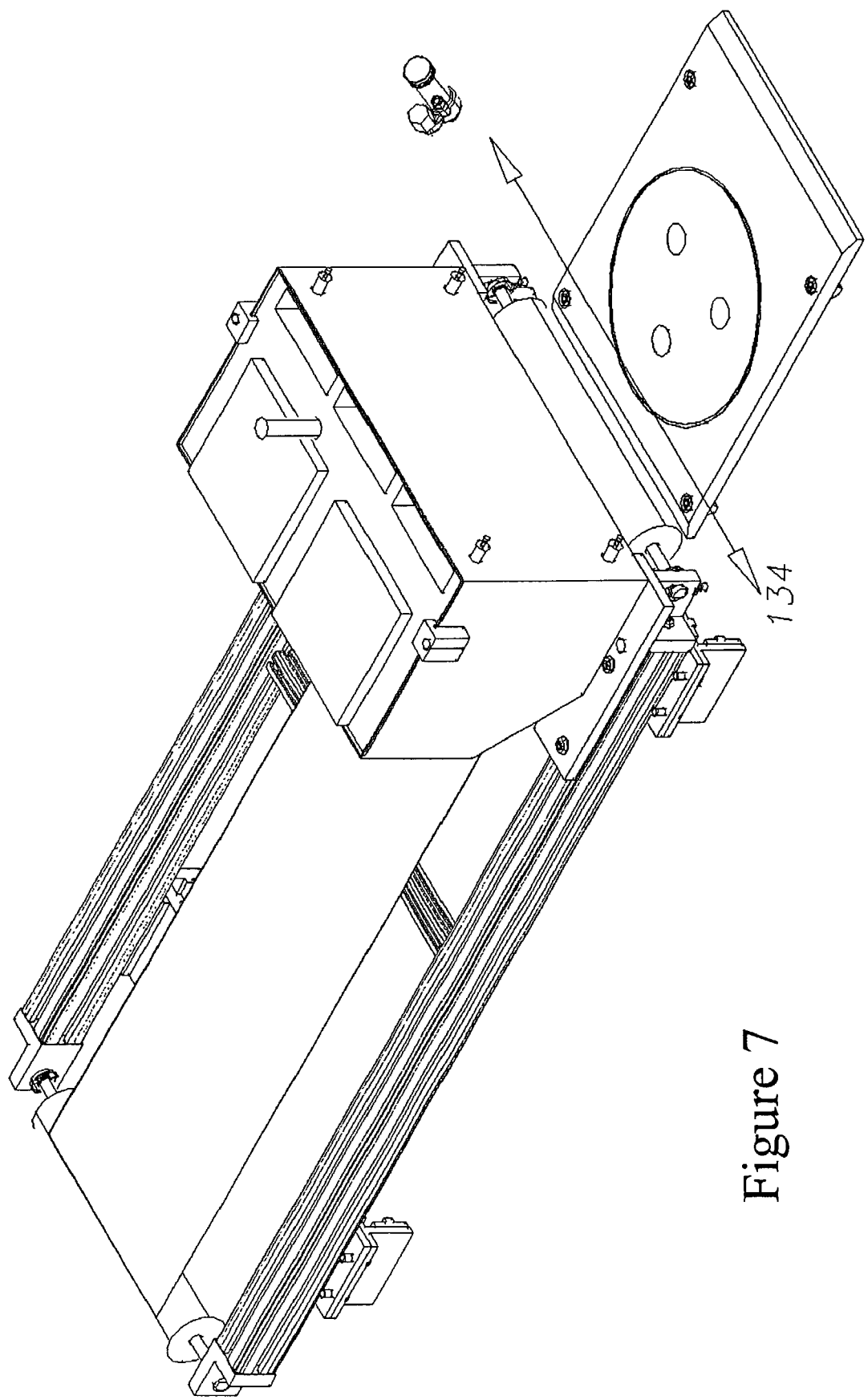
FIG. 7 illustrates a schematic drawing of an embodiment of a replication machine and the movement of 134 of an applicator tool 130.

FIG. 8 and figure illustrates the shuttle assembly 102 in the initial position where the tool plate 114 is uncovered by the substrate roll section 210. At this time, an applicator tool 130 is positioned between the substrate material and the tool plate 114. As the shuttle mechanism 102 rolls over the tool plate 114 (see, e.g., FIG. 5), the applicator tool 130 applies a liquid coating material between the substrate roll section 210 and the pattern, such as a grating pattern, on the tool mounted on the tool plate 114. In one embodiment, an applicator tool 130 applies a sufficient amount of liquid coating when the shuttle mechanism is in the initial position on a portion of the pattern so that as the shuttle mechanism 102 advances completely over the tool plate 114 (see, e.g., FIG. 6), enough liquid coating is applied to cover the entire surface area of the tool 116, such as a master wafer, to form a substrate roll section with a liquid layer. For example, the applicator tool can apply the liquid coating starting from one end of pressure roller 112 to the opposite end of pressure roller 112. See, e.g., FIG. 7.

Accordingly, once the applicator tool 130 has passed from one end of the pressure roller to the other end, then the applicator tool 130 can be temporarily placed to the side of the tool plate in order to provide clearance for the shuttle mechanism 102. The pattern on the tool is transferred to the liquid coating material on the substrate roll section 210 by rolling the pressure roller 112 over the liquid coating on the substrate roll section 210 to create a pattern coated substrate roll section.

In another embodiment, the liquid is applied to the entire pattern on the tool. Accordingly, the pattern on the tool transfers the pattern to the liquid coating material on the substrate roll section 210 as the pressure roller 112 applies pressure to the substrate roll section 210, the liquid coating and the tool. As the shuttle mechanism 102 travels to the end position, the substrate section 210 covers the tool plate 114. As a result, a pattern coating layer is created on the substrate. Further, air bubbles that might be trapped between the substrate roll section 210 and the tool plate 114 are removed as the pressure roller 112 rolls over the substrate roll section 210. Consequently, the pattern on the tool can be transferred with fewer air bubbles.

The liquid coating material can be any liquid for forming a pattern, such as a grating, on the substrate material. In one embodiment, the liquid coating material can be a solvent free radiation addition polymerizable crosslinkable material. Additionally, the liquid coating material can be an epoxy, a polymer, a cement, a resin, or any combination of these materials. Further, the crosslinkable material can be an acrylate epoxy ureathane based material.

As the shuttle mechanism 102 shuttles between the initial and final positions as shown in FIGS. 8 and 9, substrate roll 118 and take-up spool 120 remain stationary. As a result, the substrate roll section 210 travels with pressure roller 112 as the linear shuttle mechanism 102 rolls over tool plate 114. After the pressure roller 112 has completed the full motion of forward travel, the pressure roller 112 stops at the final position. Then, the pressure roller 112 reverses direction and unrolls (retracts) towards the initial position of the tool plate 114. Since the substrate roll section 210 travels with the pressure roller 112 during unrolling, the substrate roll section 210 is removed from the tool plate 114 by peeling. Once the shuttle mechanism 102 has completed a fill cycle of rolling and unrolling over tool plate 114, the shuttle mechanism 102 returns to the initial position as shown in FIG. 8. The substrate roll 118 and the take-up spool 120 can then advance causing the substrate material to advance to the next substrate roll section 210. In one embodiment, the substrate material is advanced while the shuttle mechanism 102 remains stationary in the initial position. As previously stated, the applicator tool 130 can be temporarily placed to the side of the tool plate 114. As a result, the applicator tool 130 is not shown in FIG. 9 because the applicator tool 130 is behind the shuttle mechanism 102 in FIG. 9. Other configurations can be used as well.

A hardening process cures the pattern coating layer on the substrate roll section 210 producing a cured pattern substrate. The hardening activator 108 hardens the liquid coating material as the linear roller 102 rolls over the substrate. In the case where the liquid coating material is epoxy, the hardener 108 is a UV light to cure the epoxy. Alternatively, the hardening activator 108 can be a source of heat, or an electron beam. However, any appropriate type of hardening activator or device can be used to harden or cure the liquid coating material. The hardening activator 108 cures the pattern coated substrate roll section 210 as shown in FIG. 9 as the pressure roller 102 rolls over the substrate roll section 210. In the case of the liquid coating being epoxy, a cured epoxy layer with the pattern is formed on the substrate roll section 210.

In one embodiment, the hardening activator 108 is ultra violet light passing through the substrate material above the shuttle mechanism 102 and onto the substrate roll section 210 below the shuttle mechanism 102. The ultra violet light cures the liquid coating after the pressure roller 112 has rolled over the advancing substrate material 210 as shown in FIG. 9. In another embodiment, the hardening activator 108 radiates with ultra violet light, heat, electron beam or other method directly onto the substrate material 210 without passing through the substrate material on top of the shuttle mechanism 102. For example, the radiated light, heat, or beam can be placed within rather than above the shuttle mechanism 102.

FIG. 9 illustrates the shuttle mechanism 102 covering the tool plate 114 after having fully rolled over the tool plate 114. As previously mentioned, as the linear roller 102 unrolls over the tool plate 114, the substrate sheet 210 is peeled off the tool plate 114. Accordingly, detachment of the cured pattern substrate roll section 210 from the tool plate 114 is performed, for example, by retracting or unrolling the shuttle mechanism 102 from the tool plate 114. Therefore, the shuttle mechanism 102 unrolls to delaminate the pattern coating layer on the substrate roll section 210 from the master wafer on the tool plate 114.

As the shuttle mechanism 102 unrolls, the substrate roll section 210 exposes a cured pattern on the substrate sheet to form a cured pattern substrate. The cured pattern substrate with the desired pattern rolls toward shuttle roller 110. The cured pattern substrate then is fed around second directional roller 128. Once the shuttle mechanism 102 returns to the initial position, the cured pattern substrate then is rolled on to the take-up spool 120 as previously described by advancing the substrate material and by rolling the take-up spool 120 to form a coated substrate roll.

As shown in FIGS. 8 and 9, the tool plate 114 can be substantially flat so that the shuttle mechanism 102 travels linearly in a plane parallel to the surface of tool plate 114. A flat tool plate 114 can be formed by combining one or more tools, such as flat silicon master wafers.

Alternatively, the tool plate 114 and tool can be curved. For example, a master wafer and tool plate 114 can be made of nickel or any other appropriate flexible material for forming a curved master wafer. Accordingly, the grating from the master wafer can be transferred to a nickel plate that can be curved into an appropriate shape. A curved master wafer can be used, for example, to reduce the peeling angle created between the pressure roller 112 and the substrate material 210. By reducing the peeling angle, any damage to the cured layer on the substrate material 210 can be reduced or minimized. As the shuttle mechanism 102 advances over the tool plate 114, pressure roller 112 follows the contour of the curved tool plate 114.

As described above, the substrate material can be advanced in order to expose a new section of the substrate roll section 210. The process using the steps described above to create a pattern on the substrate material can also be repeated on the next section of the substrate material.

In one embodiment the substrate material has a protective lining in order to protect the substrate while on the substrate roll 118 and while unrolling from the substrate roll 118. In another embodiment, substrate roll 118 can be lined on both sides. Alternatively, the substrate roll 118 has no lining. The machine 10 can then remove the one or more protective linings as the substrate sheet is unrolled from the substrate roll 118.

As previously described, a high refractive index dielectric film can be applied to the pattern coating layer to provide a dielectric film layer that has a higher refractive index than the "cured pattern" substrate. In a preferred embodiment of the invention the cured liquid layer and the substrate have a substantially similar refractive index which is lower than the refractive index of the high refractive index dielectric film layer. The film can be added for example by sputter deposition techniques. The dielectric film can be applied onto the substrate material before it is collected onto the take-up spool 120. Alternatively, the film can be added by removing the coated substrate roll 120, unrolling the coated substrate and adding the film. Accordingly, the process of adding the dielectric film can be integrated into the steps above, or can be a separate process. For example, the film can be added by passing the coated substrate through a sputter deposition chamber.

Subwavelength Structured Surface (SWS) Biosensor

The microreplicating techniques of the invention can be used to make a subwavelength structured surface (SWS), such as a colorimetric resonant diffractive grating surface. See U.S. application Ser. Nos. 10/058,626 and 10/059,060. Such a grating surface can be used to create a sharp optical resonant reflection at a particular wavelength that can be used to track with high sensitivity the interaction of biological materials, such as specific binding substances or binding partners or both. The colormetric resonant diffractive grating surface acts as a surface binding platform for specific binding substances.

Subwavelength structured surfaces are an unconventional type of diffractive optic that can mimic the effect of thin-film coatings. (Peng & Morris, "Resonant scattering from two-dimensional gratings," *J. Opt. Soc. Am. A*, Vol. 13, No. 5, p. 993, May; Magnusson, & Wang, "New principle for optical filters," *Appl. Phys. Lett.*, 61, No. 9, p. 1022, August, 1992; Peng & Morris, "Experimental demonstration of resonant anomalies in diffraction from two-dimensional gratings," *Optics Letters*, Vol. 21, No. 8, p. 549, April, 1996). A SWS structure contains a one-, two- or three-dimensional grating in which the grating period is small compared to the wavelength of incident light so that no diffractive orders other than the reflected and transmitted zeroth orders are allowed to propagate. A SWS structure can comprise an optical grating sandwiched between a substrate layer and a cover layer that fills the grating. Optionally, a cover layer is not used. When the effective index of refraction of the grating region is greater than the substrate or the cover layer, a waveguide is created. When a filter is designed properly, incident light passes into the waveguide region and propagates as a leaky mode. An optical grating structure selectively couples light at a narrow band of wavelengths into the waveguide. The light propagates only a very short distance (on the order of 10-100 micrometers), undergoes scattering, and couples with the forward- and backward-propagating zeroth-order light. This highly sensitive coupling condition can produce a resonant grating effect on the reflected radiation spectrum, resulting in a narrow band of reflected or transmitted wavelengths. The depth and period of the one-, two- or three-dimensional grating are less than the wavelength of the resonant grating effect.

The reflected or transmitted color of this structure can be modulated by the addition of molecules such as specific binding substances or binding partners or both to the upper surface the grating surface or cover layer. The added molecules increase the optical path length of incident radiation through the structure, and thus modify the wavelength at which maximum reflectance or transmittance will occur.

In one embodiment, a biosensor, when illuminated with white light, is designed to reflect only a single wavelength or a narrow band of wavelengths. When specific binding substances are attached to the surface of the biosensor, the reflected wavelength is shifted due to the change of the optical path of light that is coupled into the grating. By linking specific binding substances to a biosensor surface, complementary binding partner molecules can be detected without the use of any kind of fluorescent probe or particle label. The detection technique is capable of resolving changes of, for example, ~0.1 nm thickness of protein binding, and can be performed with the biosensor surface either immersed in fluid or dried.

A detection system can include, for example, a light source that illuminates a small spot of a biosensor at normal incidence through, for example, a fiber optic probe, and a spectrometer that collects the reflected light through, for example, a second fiber optic probe also at normal incidence. Because no physical contact occurs between the excitation/detection system and the biosensor surface, no special coupling prisms are required and the biosensor can be easily adapted to any commonly used assay platform including, for example, microtiter plates and microarray slides. A single spectrometer reading can be performed in several milliseconds; it is thus possible to quickly measure a large number of molecular interactions taking place in parallel upon a biosensor surface, and to monitor reaction kinetics in real time.

This technology is useful in applications where large numbers of biomolecular interactions are measured in parallel, particularly when molecular labels would alter or inhibit the functionality of the molecules under study. High-throughput screening of pharmaceutical compound libraries with protein targets, and microarray screening of protein-protein interactions for proteomics are examples of applications that require the sensitivity and throughput afforded by the compositions and methods of the invention.

FIG. 1 is a diagram of an example of a colorimetric resonant diffractive grating biosensor. In FIG. 1, $n_1$ represents a grating. $n_2$ represents the refractive index of a high refractive index dielectric layer. Layer thicknesses (i.e. cover layer, one or more specific binding substances, or an optical grating) are selected to achieve resonant wavelength sensitivity to additional molecules on the top surface. The grating period is selected to achieve resonance at a desired wavelength.

A SWS biosensor comprises an optical grating, a substrate layer that supports the grating, and one or more specific binding substances immobilized on the surface of the grating opposite of the substrate layer. Optionally, a cover layer covers the grating surface.

An optical grating made according to the invention is coated with a high refractive index dielectric film which can be comprised of a material that includes, for example, zinc sulfide, titanium dioxide, tantalum oxide, and silicon nitride. A crosssectional profile of a grating with optical features can comprise any periodically repeating function, for example, a "square-wave." An optical grating can also comprise a repeating pattern of shapes selected from the group consisting of lines, squares, circles, ellipses, triangles, trapezoids, sinusoidal waves, ovals, rectangles, and hexagons.

Sensor Characteristics

Figure 10A:
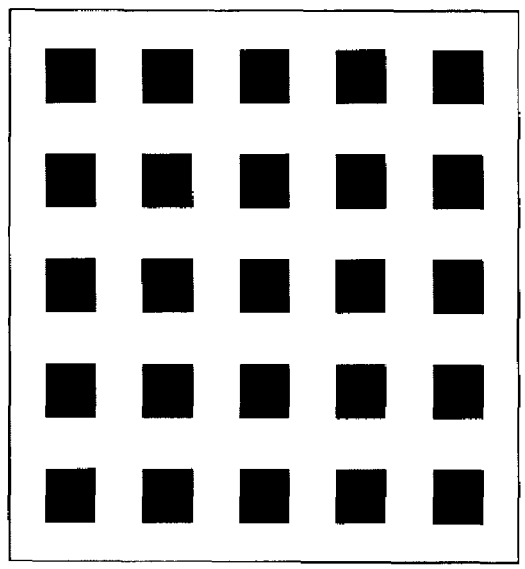
FIGS. 10A-B shows a grating comprising a rectangular grid of squares (FIG. 10A) or holes (FIG. 10B)
Figure 10B:
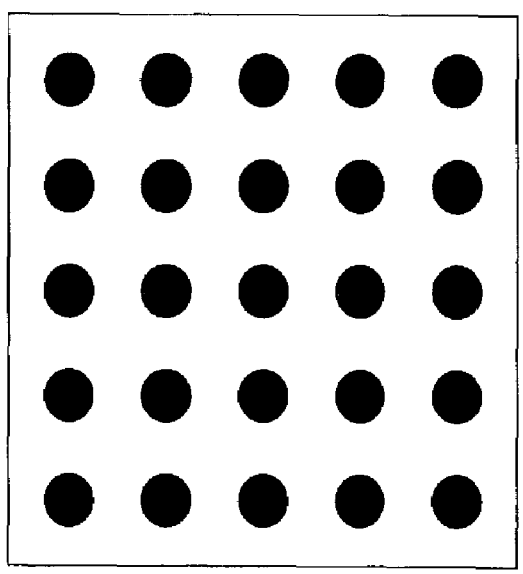

Linear gratings (i.e., one dimensional gratings) have resonant characteristics where the illuminating light polarization is oriented perpendicular to the grating period. A calorimetric resonant reflection biosensor can also comprise, for example, a two-dimensional grating, e.g., a hexagonal array of holes (see FIG. 10B) or squares (see FIG. 10A). A linear grating has the same pitch (i.e. distance between regions of high and low refractive index), period, layer thicknesses, and material properties as a hexagonal array grating. However, light must be polarized perpendicular to the grating lines in order to be resonantly coupled into the optical structure. Therefore, a polarizing filter oriented with its polarization axis perpendicular to the linear grating must be inserted between the illumination source and the biosensor surface. Because only a small portion of the illuminating light source is correctly polarized, a longer integration time is required to collect an equivalent amount of resonantly reflected light compared to a hexagonal grating.

An optical grating can also comprise, for example, a "stepped" profile, in which high refractive index regions of a single, fixed height are embedded within a lower refractive index cover layer. The alternating regions of high and low refractive index provide an optical waveguide parallel to the top surface of the biosensor.

It is also possible to make a resonant biosensor in which the high refractive index material is not stepped, but which varies with lateral position, for example, a profile in which the high refractive index material of the two-dimensional grating, is sinusoidally varying in height. To produce a resonant reflection at a particular wavelength, the period of the sinusoid is identical to the period of an equivalent stepped structure. The resonant operation of the sinusoidally varying structure and its functionality as a biosensor has been verified using GSOLVER (Grating Solver Development Company, Allen, Tex., USA) computer models.

A biosensor of the invention can further comprise a cover layer on the surface of an optical grating opposite of a substrate layer. Where a cover layer is present, the one or more specific binding substances are immobilized on the surface of the cover layer opposite of the grating. Preferably, a cover layer comprises a material that has a lower refractive index than a material that comprises the grating. A cover layer can be comprised of, for example, glass (including spin-on glass (SOG)), epoxy, or plastic.

For example, various polymers that meet the refractive index requirement of a biosensor can be used for a cover layer. SOG can be used due to its favorable refractive index, ease of handling, and readiness of being activated with specific binding substances using the wealth of glass surface activation techniques. When the flatness of the biosensor surface is not an issue for a particular system setup, a grating structure of SiN/glass can directly be used as the sensing surface, the activation of which can be done using the same means as on a glass surface.

Resonant reflection can also be obtained without a planarizing cover layer over an optical grating. For example, a biosensor can contain only a substrate coated with a structured thin film layer of high refractive index material. Without the use of a planarizing cover layer, the surrounding medium (such as air or water) fills the grating. Therefore, specific binding substances are immobilized to the biosensor on all surfaces of an optical grating exposed to the specific binding substances, rather than only on an upper surface.

In general, a biosensor of the invention will be illuminated with white light that will contain light of every polarization angle. The orientation of the polarization angle with respect to repeating features in a biosensor grating will determine the resonance wavelength. For example, a "linear grating" (i.e., a one-dimensional grating) biosensor structure consisting of a set of repeating lines and spaces will have two optical polarizations that can generate separate resonant reflections. Light that is polarized perpendicularly to the lines is called "s-polarized," while light that is polarized parallel to the lines is called "p-polarized." Both the s and p components of incident light exist simultaneously in an unfiltered illumination beam, and each generates a separate resonant signal. A biosensor structure can generally be designed to optimize the properties of only one polarization (the s-polarization), and the non-optimized polarization is easily removed by a polarizing filter.

Figure 20:
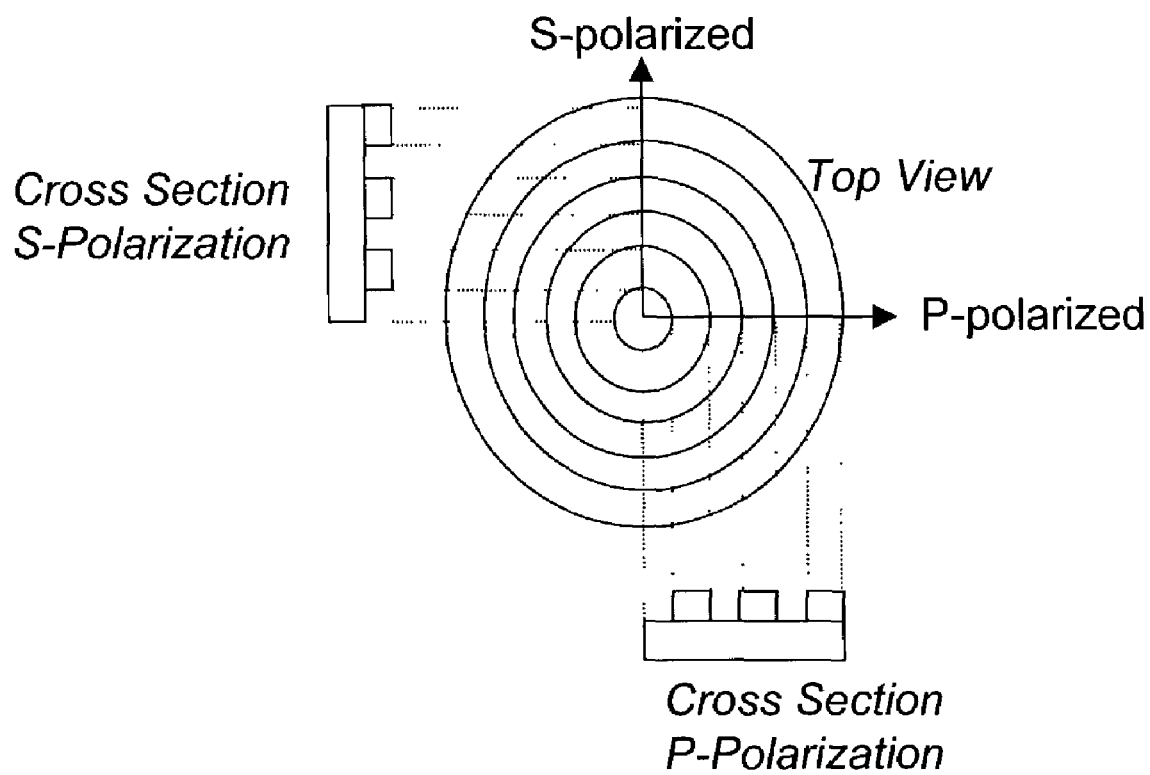
FIG. 20 shows a resonant reflection or transmission filter structure consisting of a set of concentric rings.

In order to remove the polarization dependence, so that every polarization angle generates the same resonant reflection spectra, an alternate biosensor structure can be used that consists of a set of concentric rings. In this structure, the difference between the inside diameter and the outside diameter of each concentric ring is equal to about one-half of a grating period. Each successive ring has an inside diameter that is about one grating period greater than the inside diameter of the previous ring. The concentric ring pattern extends to cover a single sensor location—such as a microarray spot or a microtiter plate well. Each separate microarray spot or microtiter plate well has a separate concentric ring pattern centered within it. See e.g., FIG. 20. All polarization directions of such a structure have the same cross-sectional profile. The concentric ring structure must be illuminated precisely on-center to preserve polarization independence. The grating period of a concentric ring structure is less than the wavelength of the resonantly reflected light. The grating period is about 0.01 micron to about 1 micron. The grating depth is about 0.01 to about 1 micron.

Figure 21:
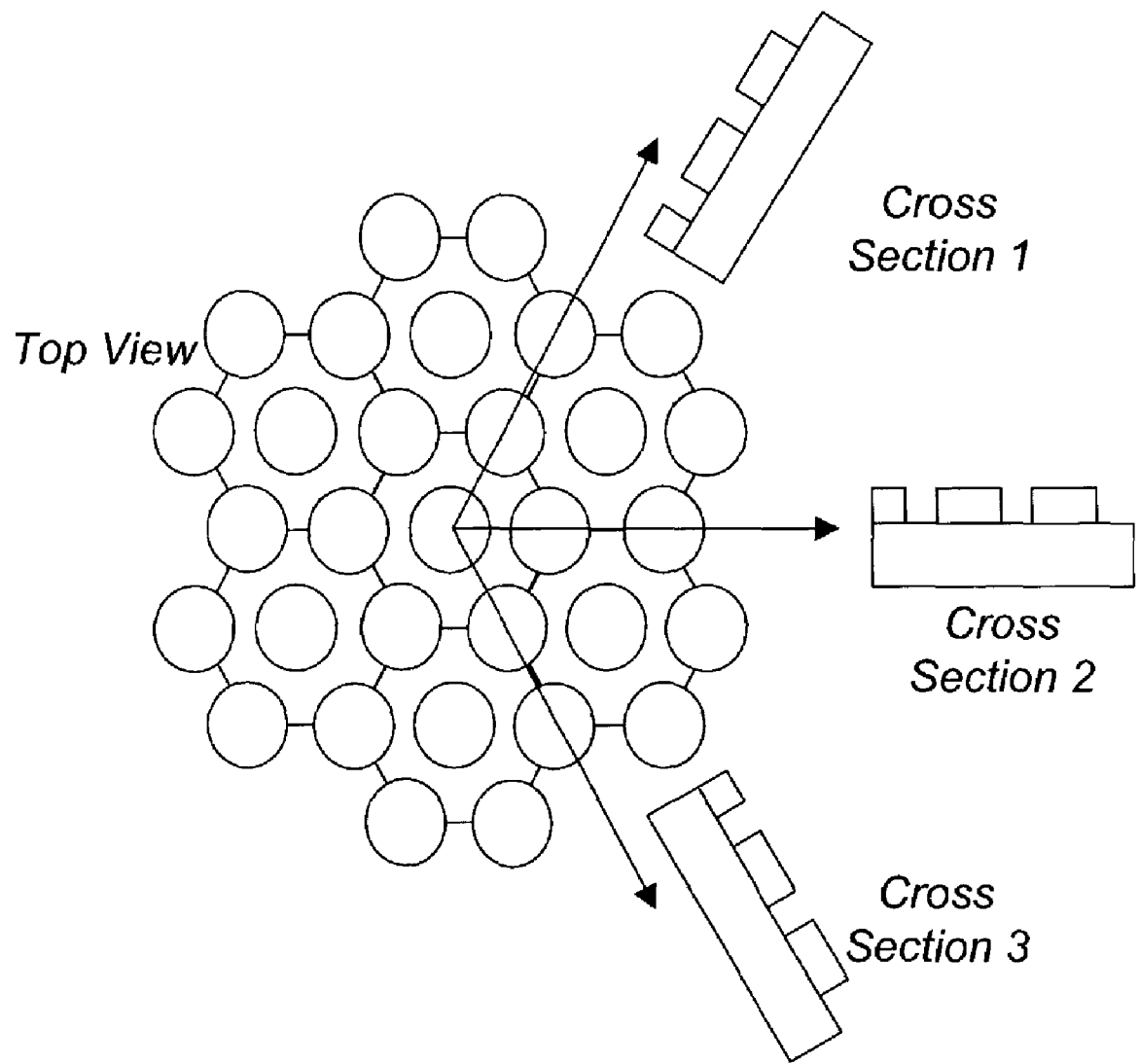
FIG. 21 shows a grid structure comprising a hexagonal grid of holes (or a hexagonal grid of posts) that closely approximates the concentric circle structure of FIG. 20 without requiring the illumination beam to be centered upon any particular location of the grid.

In another embodiment, an array of holes or posts are arranged to closely approximate the concentric circle structure described above without requiring the illumination beam to be centered upon any particular location of the grid. See e.g. FIG. 21. Such an array pattern is automatically generated by the optical interference of three laser beams incident on a surface from three directions at equal angles. In this pattern, the holes (or posts) are centered upon the corners of an array of closely packed hexagons as shown in FIG. 21. The holes or posts also occur in the center of each hexagon. Such a hexagonal grid of holes or posts has three polarization directions that "see" the same crosssectional profile. The hexagonal grid structure, therefore, provides equivalent resonant reflection spectra using light of any polarization angle. Thus, no polarizing filter is required to remove unwanted reflected signal components. The period of the holes or posts can be about 0.01 microns to about 1 micron and the depth or height can be about 0.01 microns to about 1 micron.

Another grating that can be produced using the methods of the invention is a volume surface-relief volume diffractive grating (a SRVD grating), also referred to as a three-dimensional grating. SRVD grating have a surface that reflects predominantly at a particular narrow band of optical wavelengths when illuminated with a broad band of optical wavelengths. Where specific binding substances and/or binding partners are immobilized on a SRVD grating, producing a SRVD biosensor, the reflected narrow band of wavelengths of light is shifted. One-dimensional surfaces, such as thin film interference filters and Bragg reflectors, can select a narrow range of reflected or transmitted wavelengths from a broadband excitation source, however, the deposition of additional material, such as specific binding substances and/or binding partners onto their upper surface results only in a change in the resonance linewidth, rather than the resonance wavelength. In contrast, SRVD biosensors have the ability to alter the reflected wavelength with the addition of material, such as specific binding substances and/or binding partners to the surface.

A relief volume diffractive structure can be, is a three-dimensional surface-relief volume diffractive grating. The depth and period of relief volume diffraction structures are less than the resonance wavelength of light reflected from a biosensor.

A three-dimensional surface-relief volume diffractive grating can be, for example, a three-dimensional phase-quantized terraced surface relief pattern whose groove pattern resembles a stepped pyramid a reflective material is coated over the grating. When such a coatedgrating is illuminated by a beam of broadband radiation, light will be coherently reflected from the equally spaced terraces at a wavelength given by twice the step spacing times the index of refraction of the surrounding medium. Light of a given wavelength is resonantly diffracted or reflected from the steps that are a half-wavelength apart, and with a bandwidth that is inversely proportional to the number of steps. The reflected or diffracted color can be controlled by the deposition of a high refractive index layer so that a new wavelength is selected, depending on the index of refraction of the coating.

Figure 23:
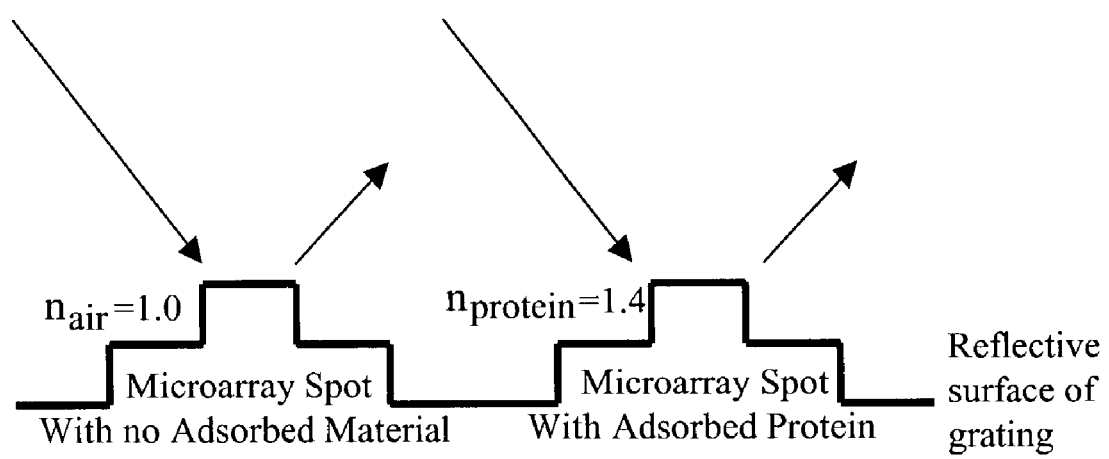
FIG. 23 shows a graphic representation of how adsorbed material, such as a protein monolayer, will increase the reflected wavelength of a biosensor that comprises a three-dimensional grating.

An example of a three-dimensional phase-quantized terraced surface relief pattern is a pattern that resembles a stepped pyramid. Each inverted pyramid is approximately 1 micron in diameter, preferably, each inverted pyramid can be about 0.5 to about 5 microns diameter, including for example, about 1 micron. The pyramid structures can be close-packed so that a typical microarray spot with a diameter of 150-200 microns can incorporate several hundred stepped pyramid structures. The relief volume diffraction structures have a period of about 0.1 to about 1 micron and a depth of about 0.1 to about 1 micron. FIG. 23 demonstrates how individual microarray locations (with an entire microarray spot incorporating hundreds of pyramids now represented by a single pyramid for one microarray spot) can be optically queried to determine if specific binding substances or binding partners are adsorbed onto the surface. When the structure is illuminated with white light, structures without significant bound material will reflect wavelengths determined by the step height of the structure. When higher refractive index material, such as binding partners or specific binding substances, are incorporated over the reflective metal surface, the reflected wavelength is modified to shift toward longer wavelengths. The color that is reflected from the terraced step structure is theoretically given as twice the step height times the index of refraction of a reflective material that is coated onto the first surface of a SRVD biosensor. A reflective material can be, for example silver, aluminum, or gold.

One or more specific binding substances, as described above, are immobilized on the reflective material of a SRVD biosensor. One or more specific binding substances can be arranged in microarray of distinct locations, as described above, on the reflective material.

Because the reflected wavelength of light from a SRVD biosensor is confined to a narrow bandwidth, very small changes in the optical characteristics of the surface manifest themselves in easily observed changes in reflected wavelength spectra. The narrow reflection bandwidth provides a surface adsorption sensitivity advantage compared to reflectance spectrometry on a flat surface.

A SRVD biosensor reflects light predominantly at a first single optical wavelength when illuminated with a broad band of optical wavelengths, and reflects light at a second single optical wavelength when one or more specific binding substances are immobilized on the reflective surface. The reflection at the second optical wavelength results from optical interference. A SRVD biosensor also reflects light at a third single optical wavelength when the one or more specific binding substances are bound to their respective binding partners, due to optical interference.

Readout of the reflected color can be performed serially by focusing a microscope objective onto individual microarray spots and reading the reflected spectrum, or in parallel by, for example, projecting the reflected image of the microarray onto a high resolution color CCD camera.

In one embodiment of the invention, an optical device is provided. An optical device comprises a structure similar to a biosensor of the invention; however, an optical device does not comprise one of more binding substances immobilized on the grating. An optical device can be used as a narrow band optical filter.

Specific Binding Substances and Binding Partners

One or more specific binding substances can be immobilized on calorimetric resonant reflectance gratings produced by the methods of the invention by for example, physical adsorption or by chemical binding where a specific binding substance is bound to a calorimetric resonant reflectance grating, a biosensor is produced. A specific binding substance can be, for example, a nucleic acid, polypeptide, antigen, polyclonal antibody, monoclonal antibody, single chain antibody (scFv), F(ab) fragment, $F(ab')_2$ fragment, Fv fragment, small organic molecule, cell, virus, bacteria, or biological sample. A biological sample can be for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, or prostatitc fluid.

Preferably, one or more specific binding substances are arranged in a microarray of distinct locations on a biosensor. A microarray of specific binding substances comprises one or more specific binding substances on a surface of a biosensor such that a surface contains many distinct locations, each with a different specific binding substance or with a different amount of a specific binding substance. For example, an array can comprise 1, 10, 100, 1,000, 10,000, or 100,000 distinct locations. Such a biosensor surface is called a microarray because one or more specific binding substances are typically laid out in a regular grid pattern in x-y coordinates. However, a microarray of the invention can comprise one or more specific binding substances laid out in any type of regular or irregular pattern. For example, distinct locations can define a microarray of spots of one or more specific binding substances. A microarray spot can be about 50 to about 500 microns in diameter. A microarray spot can also be about 150 to about 200 microns in diameter. One or more specific binding substances can be bound to their specific binding partners.

A microarray on a biosensor of the invention can be created by placing microdroplets of one or more specific binding substances onto, for example, an x-y grid of locations on an optical grating or cover layer surface. When the biosensor is exposed to a test sample comprising one or more binding partners, the binding partners will be preferentially attracted to distinct locations on the microarray that comprise specific binding substances that have high affinity for the binding partners. Some of the distinct locations will gather binding partners onto their surface, while other locations will not.

A specific binding substance specifically binds to a binding partner that is added to the surface of a biosensor of the invention. A specific binding substance specifically binds to its binding partner, but does not substantially bind other binding partners added to the surface of a biosensor. For example, where the specific binding substance is an antibody and its binding partner is a particular antigen, the antibody specifically binds to the particular antigen, but does not substantially bind other antigens. A binding partner can be, for example, a nucleic acid, polypeptide, antigen, polyclonal antibody, monoclonal antibody, single chain antibody (scFv), F(ab) fragment, $F(ab')_2$ fragment, Fv fragment, small organic molecule, cell, virus, bacteria, and biological sample. A biological sample can be, for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, and prostatitc fluid.

One example of a microarray of the invention is a nucleic acid microarray, in which each distinct location within the array contains a different nucleic acid molecule. In this embodiment, the spots within the nucleic acid microarray detect complementary chemical binding with an opposing strand of a nucleic acid in a test sample.

While microtiter plates are the most common format used for biochemical assays, microarrays are increasingly seen as a means for maximizing the number of biochemical interactions that can be measured at one time while minimizing the volume of precious reagents. By application of specific binding substances with a microarray spotter onto a biosensor of the invention, specific binding substance densities of 10,000 specific binding substances/$in^2$ can be obtained. By focusing an illumination beam to interrogate a single microarray location, a biosensor can be used as a label-free microarray readout system.

Immobilization of One or More Specific Binding Substances

Immobilization of one or more binding substances onto a biosensor is performed so that a specific binding substance will not be washed away by rinsing procedures, and so that its binding to binding partners in a test sample is unimpeded by the biosensor surface. Several different types of surface chemistry strategies have been implemented for covalent attachment of specific binding substances to, for example, glass for use in various types of microarrays and biosensors. See, e.g., FIG. 11. These same methods can be readily adapted to a biosensor of the invention. Surface preparation of a biosensor so that it contains the correct functional groups for binding one or more specific binding substances is an integral part of the biosensor manufacturing process.

One or more specific binding substances can be attached to a biosensor surface by physical adsorption (i.e., without the use of chemical linkers) or by chemical binding (i.e., with the use of chemical linkers). Chemical binding can generate stronger attachment of specific binding substances on a biosensor surface and provide defined orientation and conformation of the surface-bound molecules.

Liquid-Containing Vessels

Figure 13:
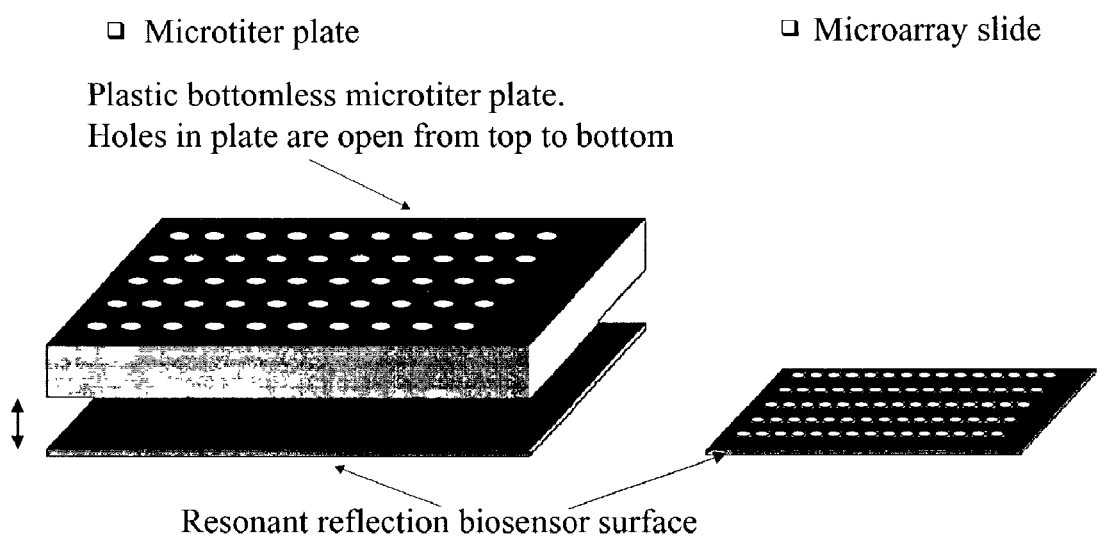
FIGS. 13A-B shows two biosensor formats that can incorporate a colorimetric resonant reflectance biosensor.

A grating of the invention can comprise an inner surface, for example, a bottom surface of a liquid-containing vessel. A liquid-containing vessel can be, for example, a microtiter plate well, a test tube, a petri dish, or a microfluidic channel. One embodiment of this invention is a biosensor that is incorporated into any type of microtiter plate. For example, a biosensor can be incorporated into the bottom surface of a microtiter plate by assembling the walls of the reaction vessels over the resonant reflection surface, as shown in FIGS. 13A and 13B, so that each reaction "spot" can be exposed to a distinct test sample. Therefore, each individual microtiter plate well can act as a separate reaction vessel. Separate chemical reactions can, therefore, occur within adjacent wells without intermixing reaction fluids and chemically distinct test solutions can be applied to individual wells.

Several methods for attaching a biosensor or grating of the invention to the bottom surface of bottomless microtiter plates can be used, including, for example, adhesive attachment, ultrasonic welding, and laser welding.

The most common assay formats for pharmaceutical high-throughput screening laboratories, molecular biology research laboratories, and diagnostic assay laboratories are microtiter plates. The plates are standard-sized plastic cartridges that can contain 96, 384, or 1536 individual reaction vessels arranged in a grid. Due to the standard mechanical configuration of these plates, liquid dispensing, robotic plate handling, and detection systems are designed to work with this common format. A biosensor of the invention can be incorporated into the bottom surface of a standard microtiter plate. See, e g., FIG. 13A. Because the biosensor surface can be fabricated in large areas, and because the readout system does not make physical contact with the biosensor surface, an arbitrary number of individual biosensor areas can be defined that are only limited by the focus resolution of the illumination optics and the x-y stage that scans the illumination/detection probe across the biosensor surface.

Methods of Using Biosensors

Biosensors can be used to study one or a number of specific binding substance/binding partner interactions in parallel. Binding of one or more specific binding substances to their respective binding partners can be detected, without the use of labels, by applying one or more binding partners to a biosensor that have one or more specific binding substances immobilized on their surfaces. A biosensor is illuminated with light and a maxima in reflected wavelength, or a minima in transmitted wavelength of light is detected from the biosensor. If one or more specific binding substances have bound to their respective binding partners, then the reflected wavelength of light is shifted as compared to a situation where one or more specific binding substances have not bound to their respective binding partners. Where a biosensor is coated with an array of distinct locations containing the one or more specific binding substances, then a maxima in reflected wavelength or minima in transmitted wavelength of light is detected from each distinct location of the biosensor.

Figure 12:
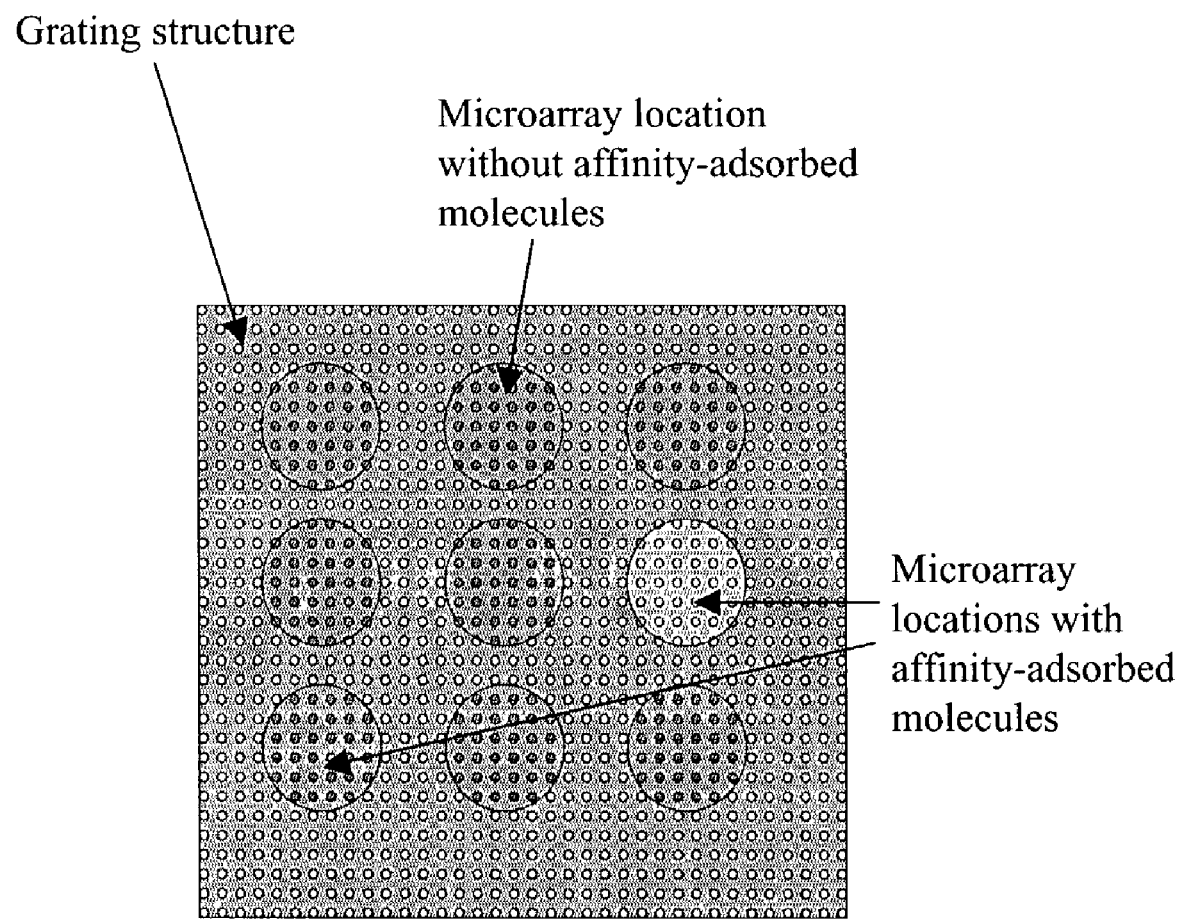
FIG. 12 shows an example of a biosensor used as a microarray.
Figure 14:
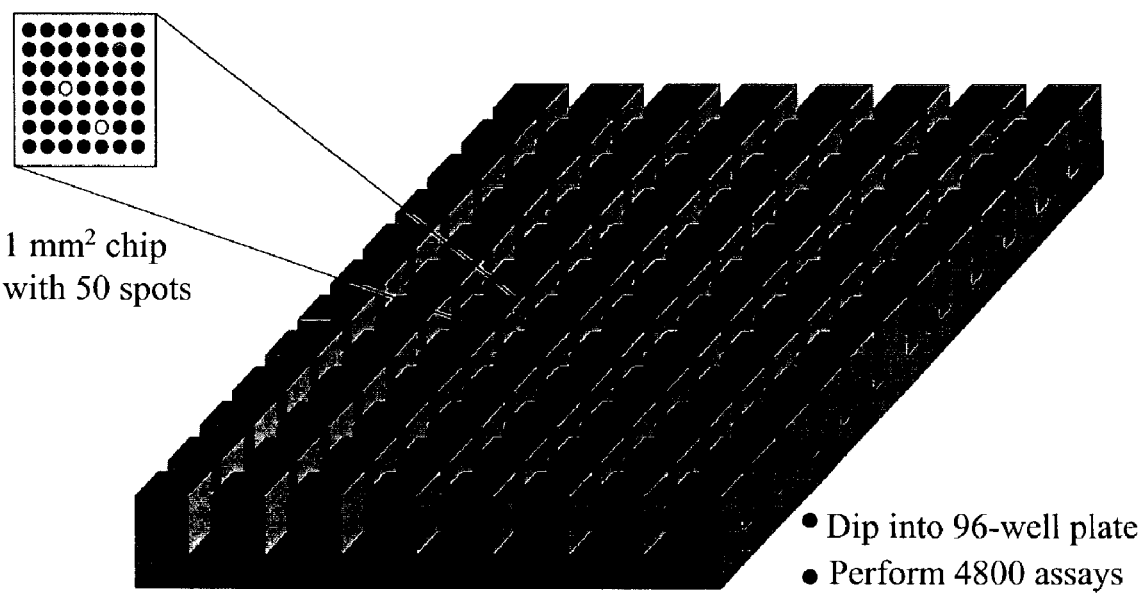
FIG. 14 shows an array of arrays concept for using a biosensor platform to perform assays with higher density and throughput.
Figure 15:
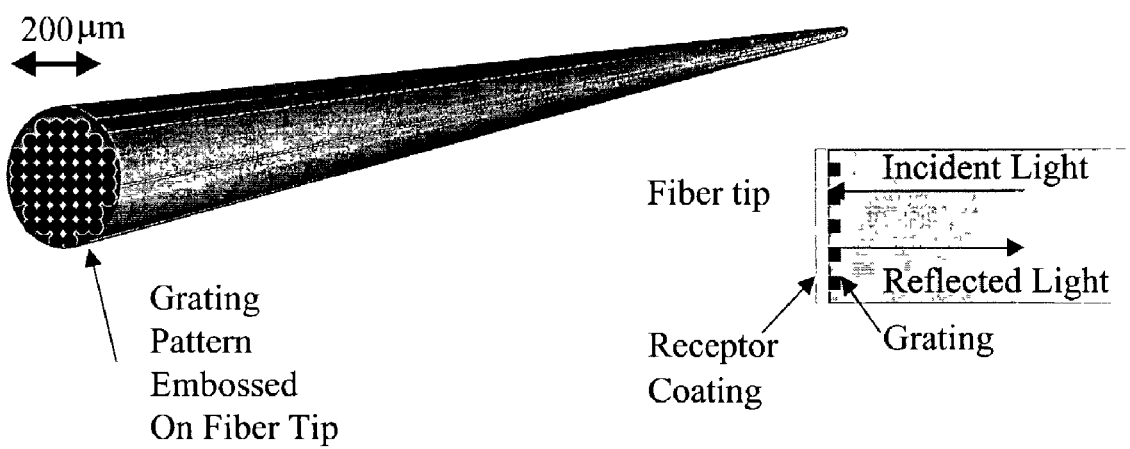
FIG. 15 demonstrates an example of a biosensor that occurs on the tip of a fiber probe for in vivo detection of biochemical substances.

In one embodiment of the invention, a variety of specific binding substances, for example, antibodies, can be immobilized in an array format onto a biosensor of the invention. See, e.g., FIG. 12. The biosensor is then contacted with a test sample of interest comprising binding partners, such as proteins. Only the proteins that specifically bind to the antibodies immobilized on the biosensor remain bound to the biosensor. Such an approach is essentially a large-scale version of an enzyme-linked immunosorbent assay; however, the use of an enzyme or fluorescent label is not required. For high-throughput applications, biosensors can be arranged in an array of arrays, wherein several biosensors comprising an array of specific binding substances are arranged in an array. See, e.g., FIG. 14. Such an array of arrays can be, for example, dipped into microtiter plate to perform many assays at one time. In another embodiment, a biosensor can occur on the tip of a fiber probe for in vivo detection of biochemical substance. See, FIG. 15.

The activity of an enzyme can be detected by applying one or more enzymes to a biosensor to which one or more specific binding substances have been immobilized. The biosensor is washed and illuminated with light. The reflected wavelength of light is detected from the biosensor. Where the one or more enzymes have altered the one or more specific binding substances of the biosensor by enzymatic activity, the reflected wavelength of light is shifted.

Additionally, a test sample, for example, cell lysates containing binding partners can be applied to a biosensor of the invention, followed by washing to remove unbound material. The binding partners that bind to a biosensor can be eluted from the biosensor and identified by, for example, mass spectrometry. Optionally, a phage DNA display library can be applied to a biosensor of the invention followed by washing to remove unbound material. Individual phage particles bound to the biosensor can be isolated and the inserts in these phage particles can then be sequenced to determine the identity of the binding partner.

For the above applications, and in particular proteomics applications, the ability to selectively bind material, such as binding partners from a test sample onto a biosensor of the invention, followed by the ability to selectively remove bound material from a distinct location of the biosensor for further analysis is advantageous. Biosensors of the invention are also capable of detecting and quantifying the amount of a binding partner from a sample that is bound to a biosensor array distinct location by measuring the shift in reflected wavelength of light. For example, the wavelength shift at one distinct biosensor location can be compared to positive and negative controls at other distinct biosensor locations to determine the amount of a binding partner that is bound to a biosensor array distinct location.

Detection Systems

A detection system can comprise a biosensor a light source that directs light to the biosensor, and a detector that detects light reflected from the biosensor. In one embodiment, it is possible to simplify the readout instrumentation by the application of a filter so that only positive results over a determined threshold trigger a detection.

A light source can illuminate a biosensor from its top surface, i.e., the surface to which one or more specific binding substances are immobilized or from its bottom surface. By measuring the shift in resonant wavelength at each distinct location of a biosensor of the invention, it is possible to determine which distinct locations have binding partners bound to them. The extent of the shift can be used to determine the amount of binding partners in a test sample and the chemical affinity between one or more specific binding substances and the binding partners of the test sample.

A biosensor can be illuminated twice. The first measurement determines the reflectance spectra of one or more distinct locations of a biosensor array with one or more specific binding substances immobilized on the biosensor. The second measurement determines the reflectance spectra after one or more binding partners are applied to a biosensor. The difference in peak wavelength between these two measurements is a measurement of the amount of binding partners that have specifically bound to a biosensor or one or more distinct locations of a biosensor. This method of illumination can control for small nonuniformities in a surface of a biosensor that can result in regions with slight variations in the peak resonant wavelength. This method can also control for varying concentrations or molecular weights of specific binding substances immobilized on a biosensor Computer simulation can be used to determine the expected dependence between a peak resonance wavelength and an angle of incident illumination. The substrate chosen was glass (refractive index=1.50). The grating is an optical pattern of silicon nitride squares ($t_2$=180 nm, $n_2$=2.01 (n=refractive index), $k_2$=0.001 (k=absorption coefficient)) with a period of 510 nm, and a filling factor of 56.2% (i.e., 56.2% of the surface is covered with silicon nitride squares while the rest is the area between the squares). The areas between silicon nitride squares are filled with a lower refractive index material. The same material also covers the squares and provides a uniformly flat upper surface. For this simulation, a glass layer was selected ($n_1$=1.40) that covers the silicon nitride squares by $t_2$=100 nm.

The reflected intensity as a function of wavelength was modeled using GSOLVER software, which utilizes full 3-dimensional vector code using hybrid Rigorous Coupled Wave Analysis and Modal analysis. GSOLVER calculates diffracted fields and diffraction efficiencies from plane wave illumination of arbitrarily complex grating structures. The illumination can be from any incidence and any polarization.

Figure 17:
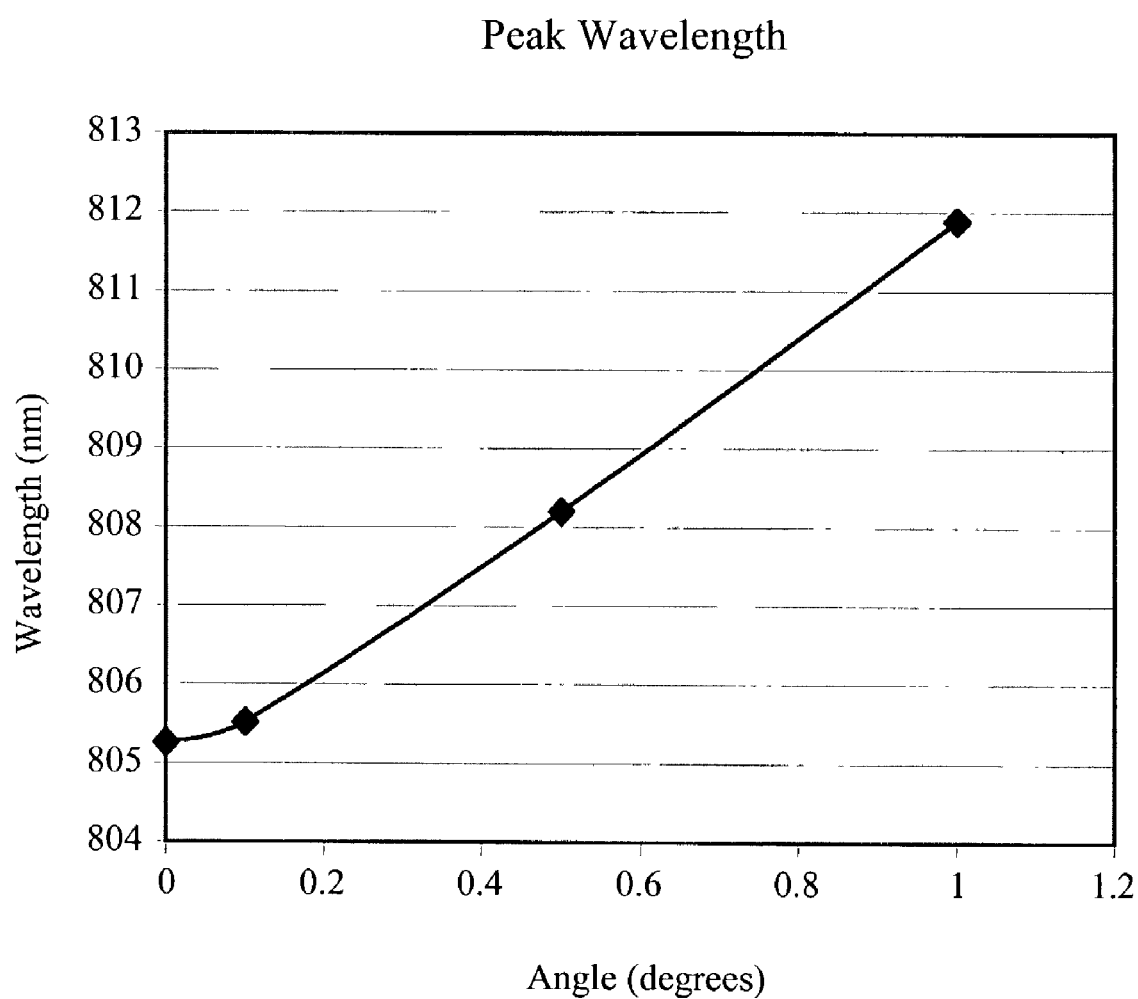
FIG. 17 shows resonance wavelength of a biosensor as a function of incident angle of detection beam.

FIG. 17 plots the dependence of the peak resonant wavelength upon the incident illumination angle. The simulation shows that there is a strong correlation between the angle of incident light, and the peak wavelength that is measured. This result implies that the collimation of the illuminating beam, and the alignment between the illuminating beam and the reflected beam will directly affect the resonant peak linewidth that is measured. If the collimation of the illuminating beam is poor, a range illuminating angles will be incident on the biosensor surface, and a wider resonant peak will be measured than if purely collimated light were incident.

Because the lower sensitivity limit of a biosensor is related to the ability to determine the peak maxima, it is important to measure a narrow resonant peak. Therefore, the use of a collimating illumination system with the biosensor provides for the highest possible sensitivity.

One type of detection system for illuminating the biosensor surface and for collecting the reflected light is a probe containing, for example, six illuminating optical fibers that are connected to a light source, and a single collecting optical fiber connected to a spectrometer. The number of fibers is not critical, any number of illuminating or collecting fibers are possible. The fibers are arranged in a bundle so that the collecting fiber is in the center of the bundle, and is surrounded by the six illuminating fibers. The tip of the fiber bundle is connected to a collimating lens that focuses the illumination onto the surface of the biosensor.

In this probe arrangement, the illuminating and collecting fibers are side-by-side. Therefore, when the collimating lens is correctly adjusted to focus light onto the biosensor surface, one observes six clearly defined circular regions of illumination, and a central dark region. Because the biosensor does not scatter light, but rather reflects a collimated beam, no light is incident upon the collecting fiber, and no resonant signal is observed. Only by defocusing the collimating lens until the six illumination regions overlap into the central region is any light reflected into the collecting fiber. Because only defocused, slightly uncollimated light can produce a signal, the biosensor is not illuminated with a single angle of incidence, but with a range of incident angles. The range of incident angles results in a mixture of resonant wavelengths due to the dependence shown in FIG. 17. Thus, wider resonant peaks are measured than might otherwise be possible.

Figure 16:
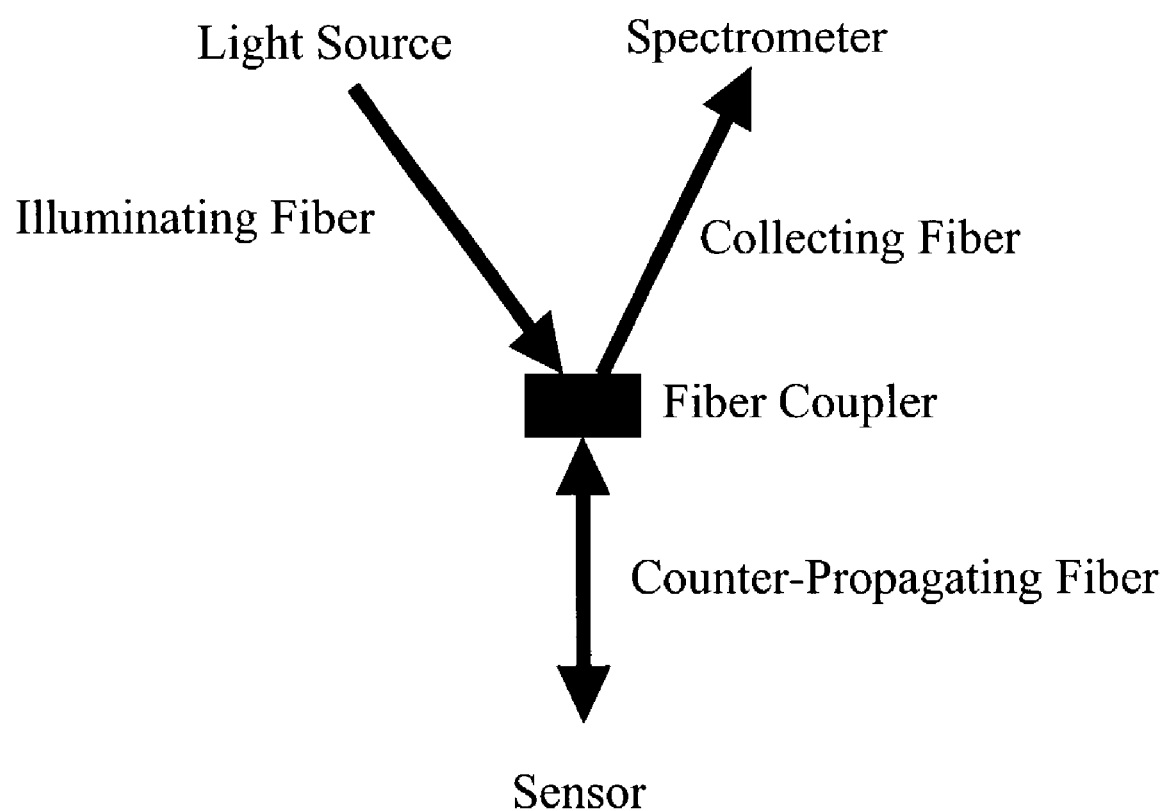
FIG. 16 shows an example of the use of two coupled fibers to illuminate and collect reflected light from a biosensor.

Therefore, it is desirable for the illuminating and collecting fiber probes to spatially share the same optical path. Several methods can be used to co-locate the illuminating and collecting optical paths. For example, a single illuminating fiber, which is connected at its first end to a light source that directs light at the biosensor, and a single collecting fiber, which is connected at its first end to a detector that detects light reflected from the biosensor, can each be connected at their second ends to a third fiber probe that can act as both an illuminator and a collector. The third fiber probe is oriented at a normal angle of incidence to the biosensor and supports counter-propagating illuminating and reflecting optical signals. An example of such a detection system is shown in FIG. 16.

Figure 18:
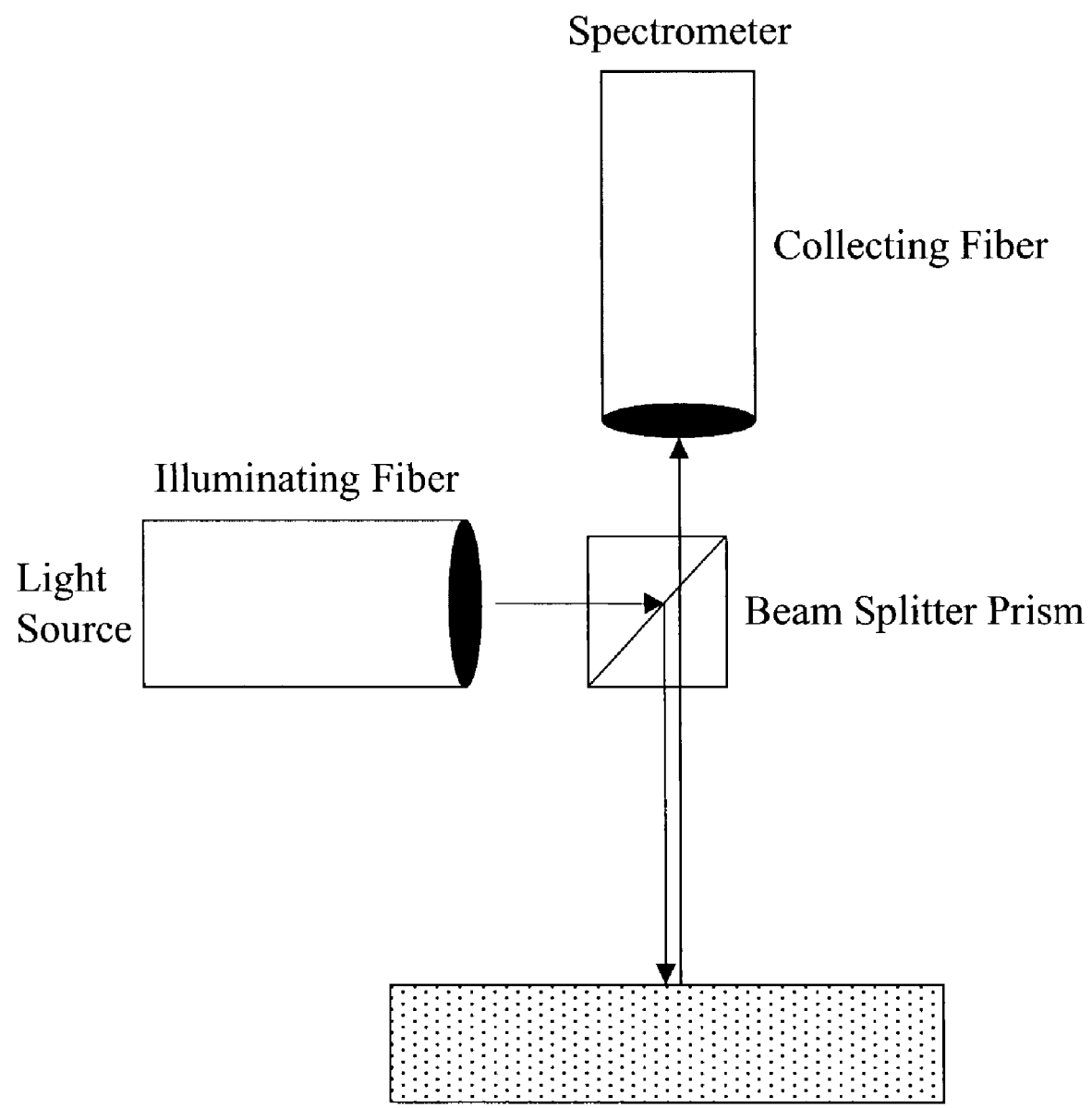
FIG. 18 shows an example of the use of a beam splitter to enable illuminating and reflected light to share a common collimated optical path to a biosensor.

Another method of detection involves the use of a beam splitter that enables a single illuminating fiber, which is connected to a light source, to be oriented at a 90 degree angle to a collecting fiber, which is connected to a detector. Light is directed through the illuminating fiber probe into the beam splitter, which directs light at the biosensor. The reflected light is directed back into the beam splitter, which directs light into the collecting fiber probe. An example of such a detection device is shown in FIG. 18. A beam splitter allows the illuminating light and the reflected light to share a common optical path between the beam splitter and the biosensor, so perfectly collimated light can be used without defocusing.

Angular Scanning

Detection systems of the invention are based on collimated white light illumination of a biosensor surface and optical spectroscopy measurement of the resonance peak of the reflected beam. Molecular binding on the surface of a biosensor is indicated by a shift in the peak wavelength value, while an increase in the wavelength corresponds to an increase in molecular absorption.

As shown in theoretical modeling and experimental data, the resonance peak wavelength is strongly dependent on the incident angle of the detection light beam. FIG. 17 depicts this dependence as modeled for a biosensor of the invention. Because of the angular dependence of the resonance peak wavelength, the incident white light needs to be well collimated. Angular dispersion of the light beam broadens the resonance peak, and reduces biosensor detection sensitivity. In addition, the signal quality from the spectroscopic measurement depends on the power of the light source and the sensitivity of the detector. In order to obtain a high signal-to-noise ratio, an excessively long integration time for each detection location can be required, thus lengthening overall time to readout a biosensor plate. A tunable laser source can be used for detection of grating resonance, but is expensive.

In one embodiment of the invention, these disadvantages are addressed by using a laser beam for illumination of a biosensor, and a light detector for measurement of reflected beam power. A scanning mirror device can be used for varying the incident angle of the laser beam, and an optical system is used for maintaining collimation of the incident laser beam. See, e.g., "Optical Scanning" (Gerald F. Marchall ed., Marcel Dekker (1991). Any type of laser scanning can be used. For example, a scanning device that can generate scan lines at a rate of about 2 lines to about 1,000 lines per second is useful in the invention. In one embodiment of the invention, a scanning device scans from about 50 lines to about 300 lines per second.

Figure 19:
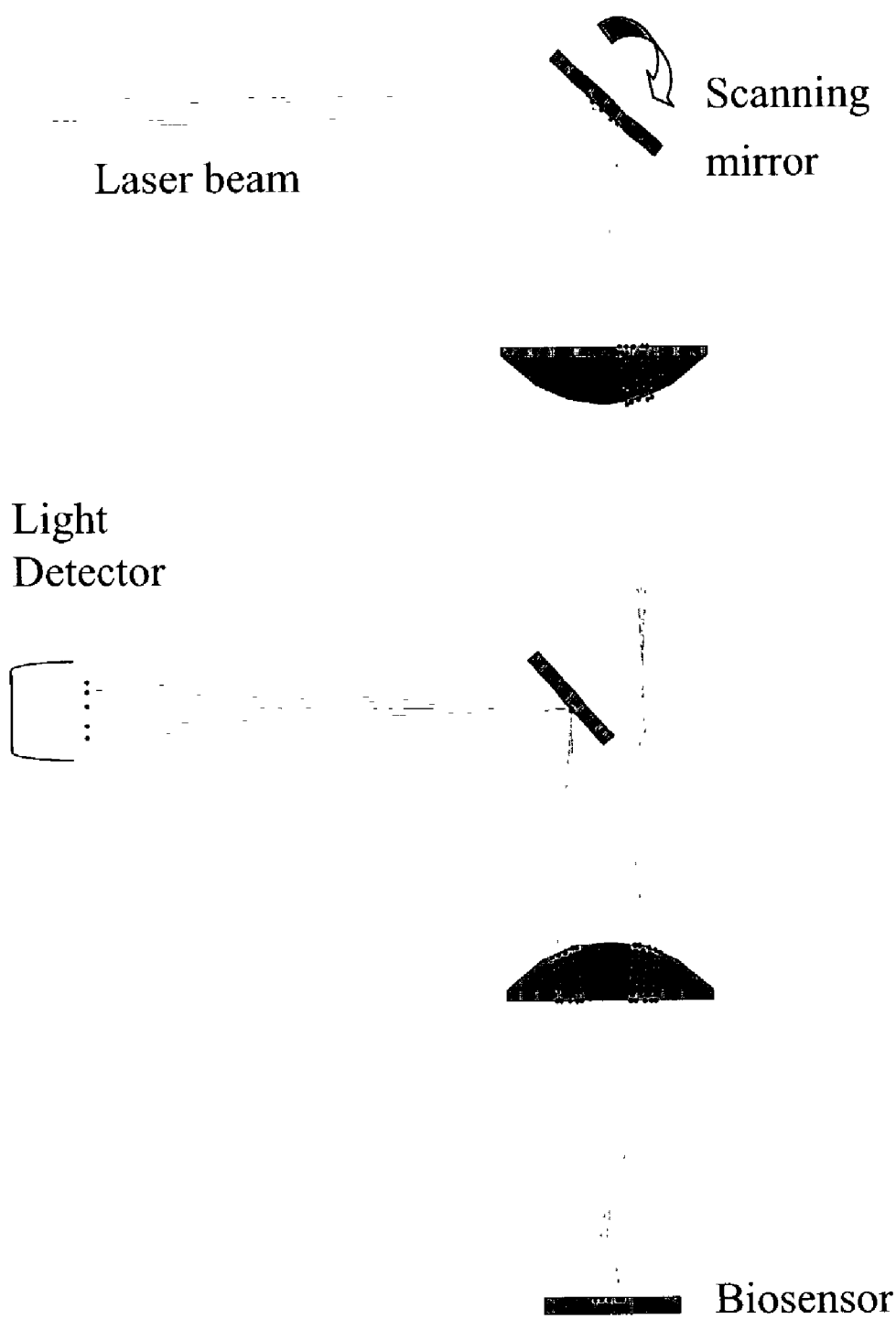
FIG. 19 shows an example of a system for angular scanning of a biosensor.
Figure 22:
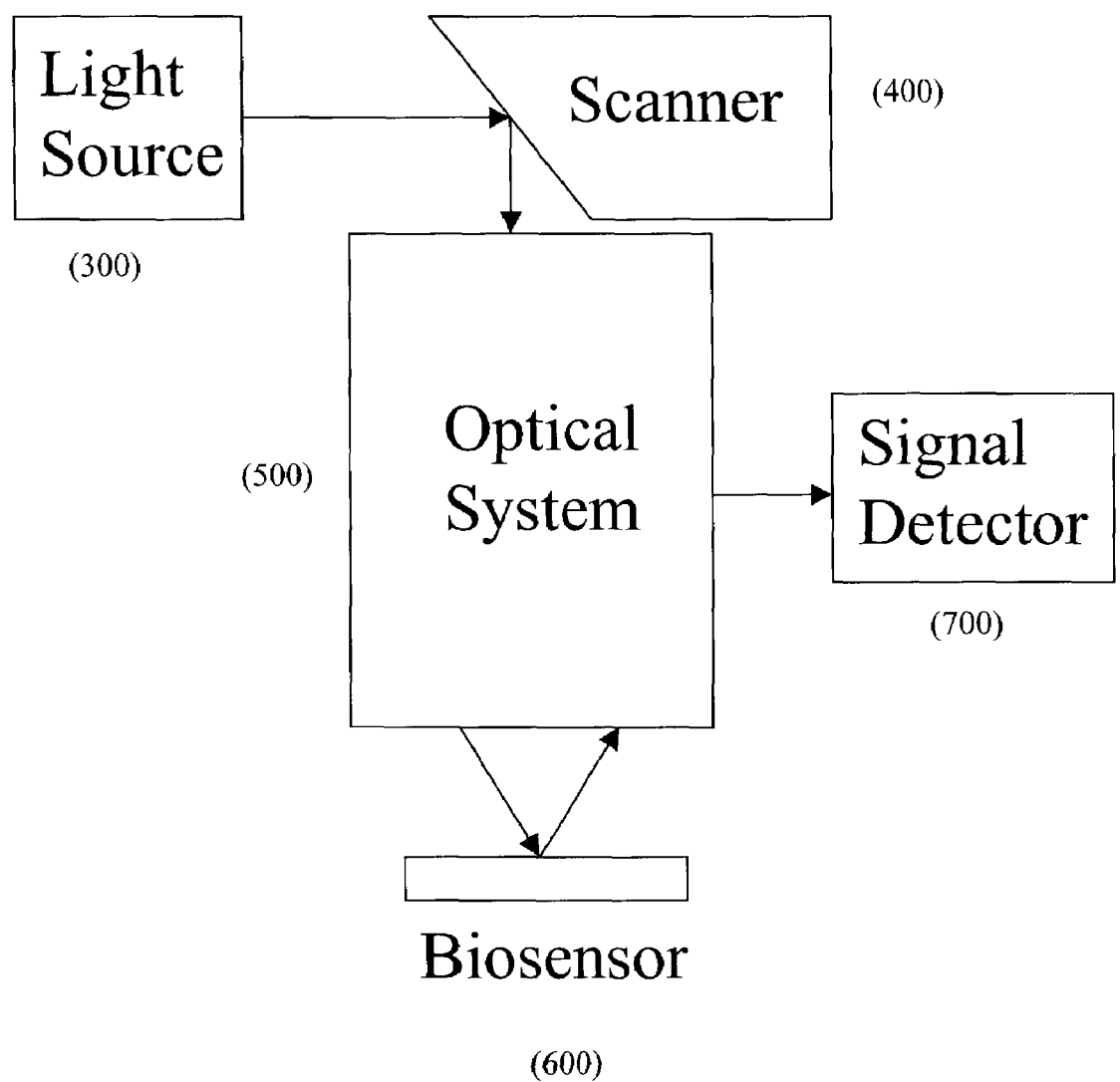
FIG. 22 shows a schematic diagram of a detection system.

In one embodiment, the reflected light beam passes through part of the laser scanning optical system, and is measured by a single light detector. The laser source can be a diode laser with a wavelength of, for example, 780 nm, 785 nm, 810 nm, or 830 nm. Laser diodes such as these are readily available at power levels up to 150 mW, and their wavelengths correspond to high sensitivity of Si photodiodes. The detector thus can be based on photodiode biosensors. An example of such a detection system is shown in FIG. 22. A light source (300) provides light to a scanner device (400), which directs the light into an optical system (500). The optical system (500) directs light to a biosensor (600). Light is reflected from the biosensor (600) to the optical system (500), which then directs the light into a light signal detector (700). One embodiment of a detection system is shown in FIG. 19, which demonstrates that while the scanning mirror changes its angular position, the incident angle of the laser beam on the surface changes by nominally twice the mirror angular displacement. The scanning mirror device can be a linear galvanometer, operating at a frequency of about 2 Hz up to about 120 Hz, and mechanical scan angle of about 10 degrees to about 20 degrees. In this example, a single scan can be completed within about 10 msec. A resonant galvanometer or a polygon scanner can also be used. The example shown in FIG. 19 includes a simple optical system for angular scanning. It consists of a pair of lenses with a common focal point between them. The optical system can be designed to achieve optimized performance for laser collimation and collection of reflected light beam.

The angular resolution depends on the galvanometer specification, and reflected light sampling frequency. Assuming galvanometer resolution of 30 arcsec mechanical, corresponding resolution for biosensor angular scan is 60 arcsec, i.e. 0.017 degree. In addition, assume a sampling rate of 100 ksamples/sec, and 20 degrees scan within 10 msec. As a result, the quantization step is 20 degrees for 1000 samples, i.e. 0.02 degree per sample. In this example, a resonance peak width of 0.2 degree, as shown by Peng and Morris (Experimental demonstration of resonant anomalies in diffraction from two-dimensional gratings, *Optics Lett.*, 21:549 (1996)), will be covered by 10 data points, each of which corresponds to resolution of the detection system.

The advantages of such a detection system includes: excellent collimation of incident light by a laser beam, high signal-to-noise ratio due to high beam power of a laser diode, low cost due to a single element light detector instead of a spectrometer, and high resolution of resonance peak due to angular scanning. All references cited in this application are incorporated herein in their entirety.

We claim:

1. A method for replicating a colorimetric resonant reflectance sensor grating pattern, the method comprising:
    (a) advancing a substrate supply roll until a substrate roll section is produced;
    (b) applying a liquid between the substrate roll section and a tool having the pattern to form a substrate roll section with a liquid layer;
    (c) rolling a shuttle mechanism having a pressure roller such that the substrate roll section with the liquid layer is rolled between the pressure roller and the tool, wherein the shuttle mechanism advances in a direction to cover the tool with the substrate roll section with a liquid layer while the substrate supply roll remains stationary,
    (d) wherein the pattern on the tool is transferred to the liquid layer to create a pattern coated substrate;
    (e) hardening the pattern coated substrate to form a cured pattern substrate;
    (f) detaching the cured pattern substrate from the tool by retracting the shuttle mechanism while the substrate supply roll remains stationary;
    (g) depositing a dielectric film on the cured pattern substrate.

2. The method of claim 1 wherein detaching the cured pattern substrate from the tool is by peeling the cured pattern substrate from the tool.

3. The method of claim 2 wherein peeling the cured pattern substrate from the tool is by unrolling the pressure roller as the shuttle mechanism retracts, wherein the cured pattern substrate is lifted by the pressure roller as the shuttle mechanism retracts.

4. The method of claim 1 wherein the tool comprises a master wafer having a master wafer grating pattern.

5. The method of claim 4 wherein the master wafer grating pattern is substantially flat and wherein the shuttle mechanism advances and retracts substantially in a plane.

6. The method of claim 4 wherein the master wafer grating pattern is curved and wherein the shuttle mechanism advances and retracts by following the curved master wafer.

7. The method of claim 4 wherein the master wafer is a master silicon wafer.

8. The method of claim 1 wherein the liquid is selected from the group consisting of an epoxy, a polymer, a cement solvent free radiation addition polymerizable crosslinikable material and a resin.

9. The method of claim 8 wherein the crosslinkable material is an acrylate epoxy ureathane based material.

10. The method of claim 1 wherein hardening the pattern coated substrate comprises exposing the pattern coated substrate to an electron beam, ultraviolet light or heat.

11. The method of claim 1 wherein the substrate supply roll comprises a substrate material selected from the group consisting of glass, plastic, polycarbonate, polyester, polyurethane, epoxy, metal, paper, composite plastic and glass, composite plastic and metal, and composite plastic and paper.

12. The method of claim 11 wherein the substrate material comprises at least one liner.

13. The method of claim 12 comprising removing the at least one liner from the substrate material as the substrate roll is advanced.

14. The method of claim 1 comprising:
advancing the cured pattern substrate onto a take-up spool to form a cured substrate roll while the shuttle mechanism remains stationary.

15. The method of claim 1 wherein the pattern has a periodic spacing wherein the spacing is between 0.1 microns to 2.0 microns.

16. The method of claim 1, wherein the pattern is a submicron grating pattern.

17. The method of claim 1 wherein the pattern has a periodic spacing wherein the spacing is between 0.2 microns to 0.6 microns.

18. The method of claim 14 wherein the dielectric film is deposited on the cured pattern substrate before the cured pattern is advanced onto a take-up spool.

19. The method of claim 14 wherein the dielectric film is deposited on the cured pattern substrate after the cured pattern is advanced onto a take-up spool.

20. The method of claim 1 wherein (a) through (g) are repeated on a next substrate roll section.

* * * * *

UNITED STATES PATENT AND TRADEMARK OFFICE
CERTIFICATE OF CORRECTION

PATENT NO. : 7,306,827 B2
APPLICATION NO. : 10/201818
DATED : December 11, 2007
INVENTOR(S) : Li et al.

It is certified that error appears in the above-identified patent and that said Letters Patent is hereby corrected as shown below:

Col. 12, Line 26, "calorimetric" should read --colorimetric--.

Col. 15, Lines 46, 49, "calorimetric" should read --colorimetric--.

Signed and Sealed this

Twelfth Day of August, 2008

JON W. DUDAS
*Director of the United States Patent and Trademark Office*